(12) United States Patent
Talbot et al.

(10) Patent No.: US 8,486,699 B2
(45) Date of Patent: Jul. 16, 2013

(54) IMMORTAL UNIPOTENT PORCINE PICM-19H AND PICM-19B STEM CELL LINES

(75) Inventors: Neil C. Talbot, Clarksville, MD (US); Thomas J. Caperna, Arnold, MD (US); Ryan Willard, Halethorpe, MD (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 1296 days.

(21) Appl. No.: 12/154,631

(22) Filed: May 23, 2008

(65) Prior Publication Data
US 2009/0291064 A1 Nov. 26, 2009

(51) Int. Cl.
*C12N 5/02* (2006.01)
*C12N 5/00* (2006.01)
*C12N 5/06* (2006.01)
*C12N 5/08* (2006.01)

(52) U.S. Cl.
USPC .......... 435/400; 435/325; 435/363; 435/395; 435/398; 435/403; 435/810

(58) Field of Classification Search
USPC .............. 435/325, 363, 395, 398, 400, 403, 435/810
See application file for complete search history.

(56) References Cited

PUBLICATIONS

Allegrucci et al., 2006, Human Reproduction Update, Vol. Advance Access published on Aug. 26, 2006, p. 1-18.*
Sato et al., 2003, Developmental Biology, vol. 260, p. 404-413.*
Abeyta et al., 2004, Human Molecular Genetics, vol. 13, No. 6, p. 601-608.*
Rao, M., 2004, Developmental Biology, vol. 275, p. 269-286.*
Nguyen et al., 2010, Advanced Drug Delivery reviews, vol. 62, p. 1175-1186.*
Fehrer et al., 2005, Experimental Gerontology, vol. 40, p. 926-930.*
Shafritz et al., 2006, Hepatology, vol. 43, p. S89-S98.*

* cited by examiner

*Primary Examiner* — Shin-Lin Chen
(74) *Attorney, Agent, or Firm* — John D. Fado; Evelyn M. Rabin

(57) ABSTRACT

Two cell lines, PICM-19H and PICM-19B, were derived from the bipotent ARS-PICM-19 pig liver stem cell line. The unipotent porcine stem cell line PICM-19H differentiates exclusively into hepatocytes and can be induced to express CYP450 enzymes. The growth rate and cell density in culture, morphological features, and hepatocyte detoxification functions, i.e., inducible CYP450 activity, ammonia clearance, and urea production of the PICM-19H cells were evaluated for their application in artificial liver devices. PICM-19H cells contain numerous mitochondria, Golgi apparatus, smooth and rough endoplasmic reticulum, vesicular bodies and occasional lipid vacuoles and display inducible CYP450 activity, clear ammonia, and produce urea in a glutamine-free medium. The data indicate that both cell lines, either together or alone, may be useful as the cellular substrate for an artificial liver device. The results demonstrate the potential for the use of PICM-19H cells in drug biotransformation and toxicity testing.

7 Claims, 25 Drawing Sheets
(5 of 25 Drawing Sheet(s) Filed in Color)

IMMORTAL UNIPOTENT PORCINE PICM-19H AND PICM-19B STEM CELL LINES

BACKGROUND OF THE INVENTION

1. Field of the Invention

This invention relates to an immortalized derivative porcine stem cell line, PICM-19H, capable of differentiating exclusively into hepatocyte cells expressing hepatocyte function, for example, inducible enzyme activity, such as cytochrome P450 (CYP450) activity; an immortalized derivative porcine stem cell line, PICM-19B, capable of differentiating exclusively into bile duct cells expressing bile duct cell function and forming a complete (confluent) cell monolayer of basolaterally polarized cells; a bioartificial liver device comprising either the PICM-19H cells or the PICM-19B cells or both, a method of using the PICM-19H and/or PICM-19B stem cell lines in a bioartificial liver device or support to alleviate liver dysfunction, a method of using the PICM-19H and/or PICM-19B stem cell lines in a screening assay to detect a compound or new chemical entity which inhibits or promotes an enzyme activity involved in the metabolism of xenobiotics in the liver and/or to detect a compound or new chemical entity which results in cytotoxicity, hepatotoxicity, or hepatic dysfunction due to the metabolism of xenobiotics and/or endogenous substrates in the liver; and a screening assay kit comprising PICM-19H cells and/or PICM-19B cells.

2. Description of the Relevant Art

Cell lines that possess in vivo-like hepatocyte functions are needed for the biological component of bioartificial liver devices that are currently in development (Strain and Neuberger. 2002. *Science* 295: 1005-1009; Chamuleau et al. 2005. *Metab. Brain Dis.* 20: 327-335). Tumor-derived cell lines, of human or animal origin, are without exception compromised in their liver functions, presumably because of their lack of normal differentiation and uncontrolled growth characteristics (Nyberg et al., 1994. *Ann. Surg.* 220(1): 59-67; Wang et al. 1998. *Cell Transplant* 7: 459-468; Kobayashi et al. 2003a. *J. Artif. Organs.* 6: 236-244; Kobayashi et al. 2003b. Keio *J. Med.* 52: 151-157; Rodriguez-Antona et al. 2002. *Xenobiotida* 32: 505-520; Filippi et al. 2004. *J. Hepatol.* 41: 599-605). Although new cell lines transfected with immortalizing transgenes are being developed and tested, there is no assurance that these cell lines won't suffer from similar problems for similar reasons (Hoekstra and Chamuleau. 2002. *Int. J. Artif. Organs.* 25: 182-191; Kobayashi et al. 2003b, supra). To date, most clinically tested bioartificial liver devices have used fresh or frozen porcine hepatocytes as the cell component in the device (Hoekstra and Chamuleau, supra; Demetriou et al. 2004. *Ann. Surg.* 239 (5): 660-670). While some efficacy in patient support has been achieved using these "liver-harvested" hepatocytes (Demetriou et al., supra), they are also compromised as cell components of bioartificial liver devices because the harvested hepatocyte cells rapidly die within the bioartificial liver device, and in addition, the cells can be under attack by the patient's pre-formed antibodies and complement factors, and further, such cell preparations are variable, and, therefore, are a potentially unsafe, cell source (Rodriguez-Antona et al., supra; Filippi et al., supra; Di Nicuolo et al. 2005. *Xenotransplantation* 2: 286-292).

Presently, most testing of new pharmacological and chemical agents in vitro for the purpose of investigating any adverse reactions with liver cells and liver cell function is performed with primary hepatocyte cultures, hepatocyte cell lines, or microsomal preparations derived from liver tissue or cells (Bertz and Granneman. 1997. *Clin. Pharmaokinet.* 32: 210-258; Yan and Caldwell. 2001. *Curr. Top. Med. Chem.* 1: 403-425; Vermeir et al. 2005. *Expert Opin. Drug Metab. Toxicol.* 1: 75-90). Microsomal preparations, while useful for some assessment, cannot be used to assess and predict cellular enzyme inductions or transport processes (Shimada et al. 1994. *J. Pharmacol. Exp. Ther.* 270: 414-423; Gómez-Lechón et al. 2004. *Curr. Drug Metab.* 5: 443-462). Fresh primary hepatocyte cultures can provide in vitro models of liver cellular function and can be prepared from a variety of species, including from specific disease state animal models (Guillouzo, A. 1998. *Environ. Health Perspect.* 106 (Suppl. 2): 511-532; Ulrichova et al. 2001. *Toxicol. Lett.* 125: 125-132; Gómez-Lechón et al., supra). However, even hepatocyte preparations of excellent quality are limited in their growth and survival in vitro, and this therefore necessitates the continual acquisition of new hepatocytes from source liver tissue (Guillouzo, supra; Hoekstra and Chamuleau, supra; Rodriguez-Antona et al., supra). Good quality human liver tissue is frequently in short supply and must always be handled as if potentially infectious (Guillouzo, supra; Hoekstra and Chamuleau, supra). Animal source liver tissue can be obtained in steady quantity and is usually not an infectious disease hazard, but even here, reproducibility problems may exist as a result of animal-to-animal genetic variation, animal health, nutritional status, and stress levels, and, perhaps most importantly, the cell culturist's skill in preparing the hepatocyte cell suspension (Guillouzo, supra; Di Nicuolo et al., supra).

To address these problems liver cell models based on hepatocyte cell lines that grow continuously, i.e., are functionally immortal, have been used. Unfortunately, immortal hepatocyte cell lines, human or otherwise, are functionally compromised as a result of their intrinsic character of unabated growth and lack of normal differentiation, and they are therefore poor model systems with which to measure normal hepatocyte metabolism; particularly the phase I and II enzymatic reactions and the cellular transport properties that are used as a basis for estimating in vivo toxicokinetics and pharmacokinetics (Guillouzo, supra; Hoekstra and Chamuleau, supra; Wilkening et al. 2003. *Drug. Metab. Dispos.* 31: 1035-1042; Yan and Caldwell, supra; Chandra and Brouwer. 2004. *Pharm. Res.* (NY) 21: 719-735). Thus, improved in vitro models for the prediction of in vivo liver biotransformation and toxicity are needed to enable faster biological evaluation of new chemical entities and to reduce controversial and costly animal testing (Bertz and Granneman, supra; Guillouzo, supra; Yan and Caldwell, supra; Chandra and Brouwer, supra).

Given the limitations of the in vitro liver cell models discussed above, it is generally accepted that a cell line that exhibits unlimited growth, and yet which differentiates normally, e.g., a liver stem cell line, would provide the best biological component for a cell based extracorporal bioartificial liver assistance device. For similar reasons, a liver stem cell line having such characteristics would also be the best in vitro model with which to conduct pharmacological and toxicological assessments of new chemical entities and would enable assessments that are standardized and repeatable.

Here, we describe the porcine liver stem cell lines of the invention, PICM-19H and PICM-19B, two derivative cell lines of the ARS-PICM-19 cell line, that fulfill these needs. The ARS-PICM-19 parental cell line and an artificial liver device comprising them have been patented in U.S. Pat. No. 5,532,156 and U.S. Pat. No. 5,866,420, respectively, and are hereby incorporated by reference in their entirety. One derivative cell line, the PICM-19H cell line, is capable of differentiating into hepatocytes and no longer exhibits the ability to differentiate and self-organize into multi-cellular bile ductules. The other cell line, PICM-19B, appears to spontaneously arise from the bile duct differentiating cells, but results in a unique cell phenotype, i.e., a dome-forming polarized epithelium, not seen within the parental ARS-PICM-19 cell line population.

SUMMARY OF THE INVENTION

We have derived (1) a unipotent porcine liver stem cell line, the PICM-19H cell line, which differentiates only into functional hepatocyte cells, from a bipotent stem cell line capable of differentiating into both hepatocytes and bile duct cells and established the PICM-19H cells as a cell line and confirmed its differentiation into hepatocytes as evidenced by its morphology, inducible CYP450 activity, serum protein production, low gamma-glutamyl transpeptidase (GGT) activity, ammonia clearance ability and urea production ability and (2) a unipotent porcine liver stem cell line, the PICM-19B cell line, which differentiates only into functional bile duct cells (cholangiocytes), from a bipotent stem cell line capable of differentiating into both hepatocytes and bile duct cells and established the PICM-19B cells as a cell line and shown that the cells form confluent (complete) cell monolayers in culture, are basolaterally polarized cells exhibiting basal membrane fluid transport, have high GGT activity and have greatly reduced serum protein production.

In accordance with this discovery, it is an object of the invention to provide an immortalized derivative porcine stem cell line capable of differentiating exclusively into hepatocyte cells expressing hepatocyte functions, namely, inducible enzyme activity involved in the metabolism of xenobiotics.

It is another object of the invention to provide the unipotent PICM-19H stem cell line wherein the major enzyme activity is CYP450 activity, including CYP1A1, CYP1A2 or CYP3A activity. Other characteristics of PICM-19H cells are low levels of GGT activity, serum protein production, urea production, and ability to clear ammonia.

It is yet another object of the invention to provide the unipotent PICM-19H stem cell line wherein the cell culture is deposited as ATCC PTA-9174.

It is an additional object of the invention to provide the unipotent porcine stem cell line which differentiates only into cholangiocytes expressing bile duct function, namely vectorial fluid transport.

It is a further object of the invention to provide the PICM-19B stem cell line which form confluent cell monolayers of basolaterally polarized cells exhibiting basal membrane fluid transport and have high GGT activity, low CYP450 activity, and no serum protein production.

It is yet another object of the invention to provide the unipotent PICM-19B stem cell line wherein the cell culture is deposited as ATCC PTA-9173, It is an object of the invention to provide a method of culturing the PICM-19H and PICM-19B stem cells with or without feeder cells.

It is an object of the invention to provide a method of culturing the PICM-19H and PICM-19B stem cells under serum-free conditions.

It is still another object of the invention to provide a method of using the unipotent PICM-19H and PICM-19B stem cell lines in a screening assay to detect a compound which inhibits or promotes an enzyme activity involved in the metabolism of xenobiotics in the liver, or which inhibits or promotes the expression of a gene encoding an enzyme involved in the metabolism of xenobiotics in the liver.

It is another object of the invention to provide a method of using the unipotent PICM-19H and PICM-19B stem cell lines in a screening assay to detect a compound which results in cytotoxicity due to the metabolism of xenobiotics and/or endogenous substrates.

It is yet another object of the invention to provide a method of using the unipotent PICM-19H and PICM-19B stem cell lines in a screening assay to detect a compound which results in carcinogenicity due to the metabolism of xenobiotics and/or endogenous substrates.

It is still another object of the invention to provide a method of using the unipotent PICM-19H and PICM-19B stem cell lines in a screening assay to detect a compound which results in mutagenicity due to the metabolism of xenobiotics and/or endogenous substrates.

Another object of the invention is to provide a method of using the unipotent PICM-19H and PICM-19B stem cell lines in a screening assay to detect a compound which results in hepatotoxicity due to the metabolism of xenobiotics and/or endogenous substrates.

An additional object of the invention is to provide a method of using the unipotent PICM-19H and PICM-19B stem cell lines in a screening assay to detect a compound which results in hepatic dysfunction.

A further object of the invention is to provide a method of using the unipotent PICM-19H and PICM-19B stem cell lines in a bioartificial liver device, such as a hollow fiber bioreactor, to extracorporally treat body fluids such as whole blood, blood plasma, and isotonic lavage-peritoneal fluid of individuals in need of such treatment to alleviate liver dysfunction.

A still further object of the invention is to provide a method of using cultures of the unipotent PICM-19H and PICM-19B stem cell lines attached to microbeads, attached to inorganic or organic porous supports, attached to hollow-fibers or encapsulated in hydrogel-based supports to treat body fluids, such as whole blood, blood plasma, and peritoneal fluids of individuals in need of such treatment to alleviate liver dysfunction.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 13A shows a monolayer expansion of PICM-19B-like variant cells (large arrows) as they grow out and over the parental phenotypes of biliary epithelial cells (ductal-forming; small arrows) and hepatocyte-like cells (monolayer patches of cuboidal cells with canaliculi; arrowheads). Note that these two parental or usually occurring differentiated phenotypes never approach confluency since they terminally differentiate well before that happens, as depicted here. In contrast, the variant PICM-19B-like cells will continue growing until confluency is achieved as depicted in FIG. 13B. Bar in (A) ~95 μm and Bar in (B) ~50 μm.

FIG. 23A shows a single hollow-fiber that was fixed with 4% paraformaldehyde after 14 days of perfusion culture and then stained with Hoechst nuclear-specific fluorescent stain, magnification: 100×. FIG. 23B shows a single hollow-fiber (as in FIG. 23A) with a detached portion of the PICM-19H monolayer (arrowheads) and the STO feeder cells situated underneath the PICM-19H cells and left attached to the hollow-fiber surface (individual STO nuclei are indicated by arrows), magnification: 100×

FIG. 24A depicts the STO cells excited by blue light (used to excite the GFP fluorescence). FIG. 24B shows the fluorescent nuclei of all the cells, STO and PICM-19H, because the ultraviolet light excites the Hoescht nuclear stain (light blue nuclear fluorescence) that the culture was stained with. Comparing FIG. 24B with 24A allows identification of the STO and PICM-19H cells.

DISCLOSURE OF THE INVENTION

Figure 1:
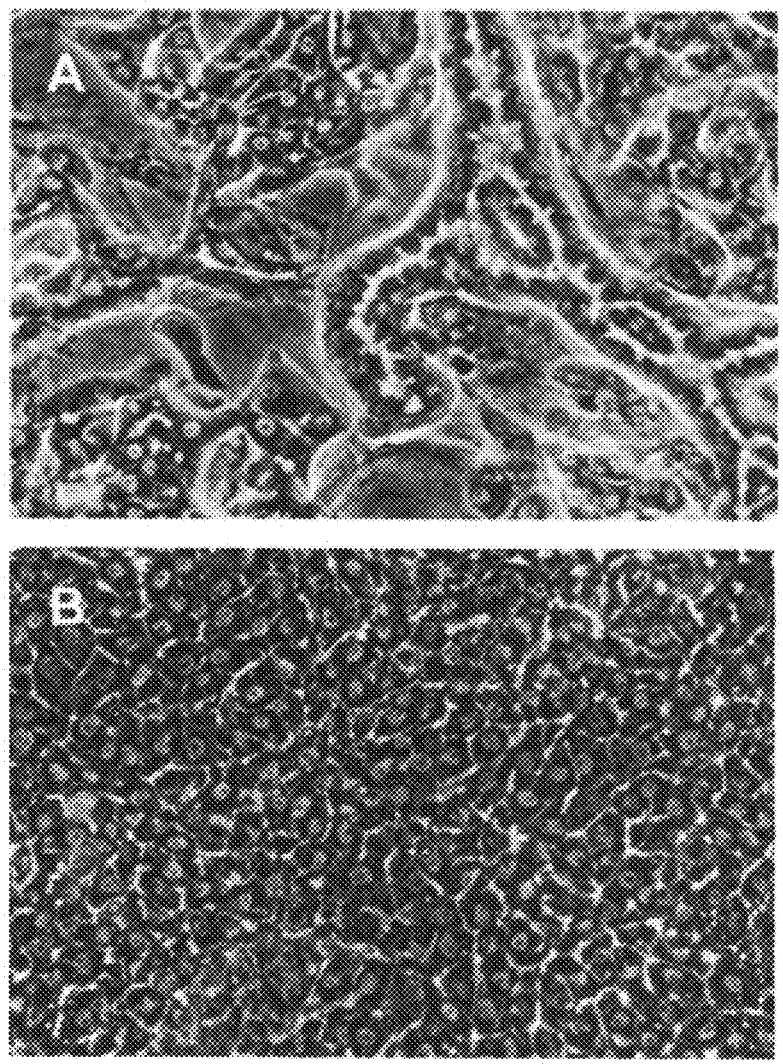
FIG. 1 shows a phase-contrast micrograph of parental ARS-PICM-19 cells culture after 3-4 wk post-passage (FIG. 1A) in comparison to a culture of the PICM-19H cells after 3 wk post-passage (FIG. 1B) at 200× magnification.

The objective of the present invention is to provide the unipotent porcine liver stem cell lines, PICM-19H, which exhibits unlimited growth, yet differentiates normally, and PICM-19B, which forms a complete monolayer with basolateral cell polarization and basal membrane fluid transport activity; a bioartificial liver device which contains the PICM-19H cell line, the PICM-19B cell line, or both, and rapid screening assays, comprising the cell lines, for estimating in vivo toxicokinetics and pharmacokinetics. The Phase I and Phase II metabolic functions of the PICM-19H and the PICM-19B cell lines have been characterized; the PICM-19H and the PICM-19B cell lines can be used to assess cellular enzyme induction and transport processes.

The ARS-PICM-19 cell line, the bipotent parental line of the unipotent PICM-19H and PICM-19B cell lines of the invention, had been derived from the in vitro culture of the totipotent embryonic stem cells of the preimplantation pig blastocyst, i.e., the epiblast cells, and was just one of many cell lines of specific cell types that spontaneously differentiated from the porcine embryonic stem cells (Talbot et al. 1993. In Vitro Cell. Dev. Biol. 29A: 543-554; Talbot et al. 1994a. In Vitro Cell. Dev. Biol. 30A: 843-850). Early in their passage history, the parental ARS-PICM-19 cells were observed to form monolayers of fetal hepatocyte-like cells as well as areas where the cells self-organized into multi-cellular ductular structures composed of cholangiocyte-like cells. ARS-PICM-19 hepatocytes have the characteristic morphology of fetal pig hepatocytes, i.e., cuboidal cells with centrally located nuclei joined by tight junctions and desmosomes to form canalicular structures between the cells (Talbot et al. 1994b. In Vitro Cell. Dev. Biol. 30A: 851-858). The ARS-PICM-19 cells could be single-cell cloned without loss of differentiation and division potential. ARS-PICM-19 cultures were found to have both inducible CYP450 activity, a marker of hepatocytes, and high GGT activity, a marker of cholangiocytes (Talbot et al. 1996a. Exp. Cell Res. 225-22-34). They also expressed alpha-fetoprotein along with albumin and other liver-specific proteins (Talbot et al. 1994a, 1996a, supra). The culture of fetal pig liver tissue (Talbot et al. 1994b, supra) and adult pig liver tissue (Talbot and Caperna. 1998. In Vitro Cell. Dev. Biol. 34A: 785-798; unpublished data) resulted in cell cultures that closely resembled the ARS-PICM-19 cells in their differentiation potential, morphology, and protein/enzyme expression. In vivo-like responses of the ARS-PICM-19 ductules to secretin and cAMP inducers were also demonstrated, i.e., basolateral to apical transport of cul-ture fluid with in vivo-like kinetics (Talbot et al. 2002. Cells Tissues Organs 171: 99-116). ARS-PICM-19 differentiation into bile duct epithelium is marked by unique in vitro intercellular and intracellular changes, i.e., self-organization into functional multi-cellular ductal structures of columnar epithelium (Talbot et al. 1994a, 1996a, 2002, supra). These in vitro-produced bile ductules closely resembled similar bile ductules that were produced in vitro from the culture of both fetal and adult pig liver tissue (Talbot et al. 1994b, 1998, supra). Thus, the ARS-PICM-19 cells had been shown to be functionally immortal (Talbot et al. 1994a, supra) and to possess characteristics of both parenchymal hepatocytes and bile duct epithelium cells (Talbot et al. 1994a, 1996a, supra). This was most directly manifest in the ARS-PICM-19 cells spontaneously stopping cell division (approximately 10 days after each passage) and differentiating into at least two strikingly different morphological phenotypes, one resembling hepatocytes and the other, self-organizing, multi-cellular, functional ductules that behaved like in vivo bile ducts (Talbot et al. 1994a, 1996a, 2002, supra).

PICM-19H and PICM-19B are two variant unipotent cell lines derived from the ARS-PICM-19 cell line described above. The PICM-19H unipotent cell line is capable of differentiating into hepatocytes and no longer exhibits the ability to differentiate and self-organize into multi-cellular bile ductules. The other cell line, PICM-19B, appears to have spontaneously arisen from the bile duct differentiating cell component of the parental ARS-PICM-19 cells and is a unique differentiated phenotype, i.e., dome-forming basolaterally polarized epithelium, not usually seen within the parental ARS-PICM-19 cell population. The isolation of these morphologically variant cell lines is described (see Example 1). The derivative cell lines were evaluated to assess to what extent they retained either hepatocyte or cholangiocyte cellular functions. Specifically, since the cells of the parental ARS-PICM-19 cell line can differentiate into either hepatocytes or bile duct cells (cholangiocytes), the nature of the cells of these particular derivative cell lines were evaluated to determine if they are more or less hepatocyte-like in their cellular functions, and whether either of them possess new unique cellular features that would enhance their utility in a bioartificial liver device and/or in vitro rapid liver toxicity assays.

As stated above, one specific use for a liver cell line is for it to act as the biological component of an extracorporeal bioartificial liver device. The bioartificial liver contains living cells, usually hepatocytes or some combination of hepatocytes and non-parenchymal accessory cells, within an ex vivo "bioreactor" through which the patient's blood or blood plasma is pumped to interact with the cells in an extracorporeal circulatory loop (Sussman and Kelly. 1995. *Scientific American* 2: 68-77; Strain and Neuberger, supra; Sen and Williams. 2003. *Seminars in Liver Disease* 23(3): 283-294). Such a device is needed for the treatment of acute liver failure because no effective treatment options are currently available that reduce the high mortality associated with this condition except liver transplantation (Sussman and Kelly, supra; Strain and Neuberger, supra; Sen and Williams, supra).

Thus, the PICM-19H and PICM-19B derivative liver cell lines of the invention are candidates for use in a bioartificial liver device because they have the particular characteristic of being immortal unipotential stem cells. That is, PICM-19H cells differentiate only into hepatocytes and do not differentiate into bile ductules. Thus, PICM-19H can provide better hepatocyte function for treatment of acute liver failure than can be provided by the parental ARS-PICM-19 cells in those situations where hepatocyte functions are the primary need, and not bile transport and conditioning functions (Sussman and Kelly, supra; Strain and Neuberger, supra; Sen and Williams, supra). Similarly, the PICM-19H cell line provides an excellent model for screening assays for the biological evaluation of new chemical entities. Inducible CYP450 activity is a marker of hepatocytes. The data set forth illustrate the specificity of the inducible CYP450 activity of the PICM-19H cell line and include a comparison to that described previously for the parental ARS-PICM-19 cell line (Talbot et al. 1996a, supra), thus demonstrating the utility of the PICM-19H cell line for in vitro toxicity testing. The potential application of PICM-19H for bioartificial liver devices is also set forth.

Qualities that make the PICM-19H cells more favorable than the parental ARS-PICM-19 cell line for application to a bioartificial liver device are that the PICM-19H cells retain critical hepatocyte functions, they are non-tumorigenic and display normal differentiation in vitro, they may be maintained in the bioartificial liver device's bioreactor for relatively long periods of time, their phenotypic stability, (i.e., no spontaneous occurrences of PICM-19B-like cells over extensive culture, approximately 450 population doublings), then pathogen-free status can be defined and routinely assessed, and they can be genetically engineered for enhancement of function.

The two PICM-19 derivatives have contrasting characteristics that make each more suitable for the cellular component of a bioartificial liver device in different ways. PICM-19H cells appear to be more "hepatocyte-like" by all measures; including cell and colony morphology, ultrastructure features, serum protein production, and metabolic enzymatic functions. The data show that the PICM-19H cells are superior in the critical hepatic functions of CYP450 activity, urea production, and ammonia clearance. However, because the PICM-19B cells grow to a greater cell density and also display these key metabolic functions (albeit at lower levels), the PICM-19B cells are a good choice for utilization in a bioartificial liver device as well, particularly where vectorial (i.e., basolateral) transport is an engineered quality of the bioartificial liver device's bioreactor. Also, PICM-19B's relative lack of serum protein secretion is of benefit in that the human patient's blood would not be exposed to so many foreign antigens (depending on the molecular weight cut-off of the dialysis membrane in the bioartificial liver device). PICM-19B's apical to basal cell membrane polarization affords an advantage in that its demonstrated directional transport (i.e., dome-formation) could potentially move toxins out of the human patient's plasma to an external waste flow circuit if the PICM-19B cells were properly configured on a bioartificial liver device's dialysis membrane. In any case and in summation, the data presented here indicate enhanced functions of the PICM-19H and PICM-19B cell lines for use in a bioartificial liver device.

Having the availability of two unipotent cell lines offers the unique opportunity to design and target the contents of the bioreactor to suit the particular functional needs of the patient. Each of the cell lines, PICM-19H and PICM-19B, can be cultured individually in the bioreactor or they can both be seeded into the bioreactor together, resulting in the opportunity to manipulate the cell numbers of each, i.e., seed in differing ratios, depending on the functions required by the patient.

It has been suggested that porcine cells would be useful for in vitro modeling of hepatic metabolic functions and as the cellular component of bioartificial liver devices due to their human hepatocyte metabolism similarities (Donato et al., 1999. *J. Hepatol.* 31: 542-549). In the present study, we have characterized the PICM-19H cell line with respect to the presence and induction of the major CYP450 activities (CYP1A, 2 and 3A). Additionally, the extent of phase 11 conjugation is shown to be significant with test substrates and comparable to adult pig hepatocytes. Known hepatotoxins, acetaminophen and aflatoxin B1, are shown to be metabolized in a dose-dependent manner. These data, combined with the other demonstrated hepatic differentiated functions and the robust culture characteristics of the PICM-19H cell line indicate that PICM-19H cells can provide a cellular component in a bioartificial liver device and also provide an improved model system for hepatic cells in in vitro toxicological testing.

CYP450 comprises a family of cellular enzymes having key enzyme activities involved in the liver-specific metabolism of xenobiotic substances, i.e., chemical substances that are foreign to the body of a living organism. Xenobiotic substances include naturally occurring compounds, drugs, environmental agents, carcinogens, insecticides, etc. CYP450 represents the class of enzymes most important from the viewpoint of distribution and functions involved in the metabolism of xenobiotics. CYP450 is a generic name for a large number of enzymatic proteins; CYP1A1, CYP1A2, CYP2A6, CYP2B6, CYP2C8, CYP2C9, CYP2C19, CYP3A (specifically CYP3A4) are known members of the CYP450 enzyme family involved in the metabolism of xenobiotics in the human liver.

In addition, a large number of xenobiotic-metabolizing enzymes are known to be induced under particular conditions. Well-known examples of inducers include polycyclic aromatic compounds such as benzo[A]pyrene, benzanthracene, 3-methylcholanthrene and dioxin which induce the expression of CYP1A1 and CYP1A2; phenobarbital and phenobarbitone which induce CYP2B (e.g., CYP2B6); and rifampicin, dexamethasone, phenyloin and phenylbutazone which induce CYP3A (C. G. Gibson et al. 1995. *New Metabolomics of Xenobiotics*, Kodansha Ltd., Tokyo, Japan).

Test compounds (new chemical entities and xenobiotic substances) include, for example, peptides, proteins, nonpeptide compounds, synthetic compounds, fermentation products, cell extracts, plant extracts, animal tissue extracts, and plasma. Thus, they include naturally occurring compounds, drugs, environmental agents, carcinogens, pesticides, herbicides, etc. These compounds may be new compounds or commonly known compounds.

Specifically, the PICM-19H or PICM-19B cells of the present invention can be treated with the test compound and compared with an untreated control PICM-19 culture to evaluate the therapeutic/preventive effects of the test compound with changes such as those in (1) an enzyme activity involved in the metabolism of xenobiotics in the liver or (2) the expression (activation) of a gene encoding an enzyme involved in the metabolism of xenobiotics in the liver, in the immortal PICM-19H or PICM-19B cells.

A test therapeutic compound identified as safe by using the screening method of the present invention can be used as a safe therapeutic/preventive or other pharmaceutical of low toxicity for diseases associated with abnormalities of the metabolism of xenobiotics in the liver (e.g., hepatic insufficiency) because of its therapeutic/preventive effects on such diseases.

A compound obtained by said screening method may have formed a salt. Said salt is exemplified by salts with physiologically acceptable acids (e.g., inorganic acids, organic acids), bases (e.g., alkali metals), etc., with preference given to physiologically acceptable acid adduct salts. Such salts include, for example, salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid).

Promotion of the activity of enzymes which metabolize xenobiotics and/or endogenous substrates can be analyzed, for example, by exposing a test substance to cells and detecting the increase in the activity of enzymes which metabolize xenobiotics and/or endogenous substrates, the increase in the amount of the enzyme and/or the increase in the amount of transcription of the gene encoding the enzyme. Specifically, this is possible by detecting the elevation of CYP450 enzyme activity, an increase in CYP450 protein content, or an increase in CYP450 mRNA in the PICM-19H or PICM-19B cells. Useful methods of detection include commonly known techniques such as assays of enzyme activities corresponding to various types of CYP450, Western blotting techniques corresponding to various CYP450 proteins, Northern hybridization techniques corresponding to various types of CYP450 mRNA, and the CYP450-specific RT-PCR methods.

Hepatotoxicity due to the metabolism of xenobiotics and/or endogenous substrates can be determined by exposing a test substance to PICM-19H or PICM-19B cells and observing or measuring the resulting cytotoxicity, or by exposing the test substance to the PICM-19 cells and subsequently administering the test substance altered by the cells to another hepatocyte, or other target cell type, and observing the changes caused thereby in the target cells.

The PICM-19H and PICM-19B unipotent cell lines as obtained in Examples 2 and 3 have been deposited as cell lines ATCC PTA-9174 and ATCC PTA-9173, respectively, on Apr. 24, 2008, under the Budapest Treaty, with the American Type Culture Collection (ATCC), located at 10801 University Boulevard, Manassas, Va. 20110.

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

EXAMPLES

Having now generally described this invention, the same will be better understood by reference to certain specific examples, which are included herein only to further illustrate the invention and are not intended to limit the scope of the invention as defined by the claims.

Example 1

Reagents Utilized for Stem Cell Culture and for Screening Assays

All cells were grown on 25 cm$^2$ tissue culture flasks (T25; Greiner, Frickenhausen, Germany). Fetal bovine serum (FBS) and iron-supplemented calf serum were purchased from Hyclone, Logan Utah. Cell culture reagents including Dulbecco's phosphate buffered saline (PBS) without Ca$^{++}$ and Mg$^{++}$, media, trypsin-EDTA (0.025% trypsin, 0.43 mM EDTA), antibiotics, non-essential amino acids, and L-glutamine were purchased from InVitrogen, Gaithersburg, Md. PICM-19H cells were grown on irradiated STO mouse fibroblast (CRL 1503, American Type Culture Collection, Rockville, Md.) feeder cell layers. Feeder-layers were prepared by exposing a suspension of STO cells to 8 krad of gamma radiation and plating the cells at 6×10$^4$ cells/cm$^2$. STO feeder-layers were maintained by refeeding with 10% DMEM every 6-7 d. The growth and differentiation medium for PICM-19 cultures was a 50:50 mixture of DMEM low glucose and Medium 199 supplemented with 10% FBS, 2-mercaptoethanol, and nucleosides as described in Talbot and Paape (1996. *Methods in Cell Science* 18: 315-327). PICM-19 cultures were refed with fresh medium every 2-3 days after passage. Cultures were routinely maintained at 37° C. and in a 3-4% CO$_2$ atmosphere.

HepG2 C3A human hepatoblastoma cells were obtained from ATCC (Manassas, Va.; CRL-10741). The cells were passaged sub-confluently in Minimal Essential Medium (MEM) supplemented with 10% FBS, 1 mM sodium pyruvate, non-essential amino acids, and antibiotics and grown at 37° C. in 5% CO$_2$. All experiments with HepG2 C3A cells were performed between passages 3 and 12.

Except where noted, all chemical reagents including aflatoxin B1, 3-methylcholanthrene (3-MC), rifampicin (rif), resorufin, phenobarbital (PHB), 7-methoxy resorufin (7-MRF), 7-ethoxyresorufin (7ERF) and dimethylsulfoxide (DMSO) were obtained from Sigma Chemical Co., St. Louis, Mo. 7-methoxy-4-(trifluoromethyl) coumarin (7MFC) and 7-benzyloxy-4-(trifluoromethyl) coumarin (7BFC) were from BD Gentest, Woburn, Mass.

Care and treatment of pigs in this study (n=3) were approved by the Institutional Animal Care and Use Committee of the U.S. Department of Agriculture. Crossbred barrows (~45 kg) were stunned by electric shock and exsanguinated. Adult pig hepatocytes were prepared from a portion of the left lateral hepatic lobe by a two-step collagenase digestion procedure as previously described (Caperna et al. 1985. *J. Anim. Sci.* 61:1576-1586; Fernández-Figares et al. 2004. *Domest. Anim. Endocrinol.* 27: 125-140). Hepatocytes ($4.5 \times 10^6$ cells) were seeded into T25 flasks pre-coated with pig tail collagen and cultured as previously described (Caperna et al. 2005. *Domest. Anim. Endocrinol.* 29: 582-592). Briefly, cells were initially maintained in William's E medium containing insulin-transferrin-selenium (ITS; Sigma) and 10% FBS. Following a 3 h attachment period, flasks were washed to remove non-attached and non-viable cells, and William's E medium containing 5% FBS and ITS was added to each flask. On the following day, flasks were washed twice and medium was replaced with 10% DMEM/199. All experiments were terminated approximately 72 h after cell isolation and initiation of cultures.

Example 2

Establishment of PICM-19H Stem Cell Line

The PICM-19H cell line was established from a T25 mass culture of parental ARS-PICM-19 cells, i.e., approximately one million cells, that were subjected to hypothermic selection (33-34° C.) for approximately 3 wk at passage 37. The PICM-19H cell line was derived from approximately 50-100 cells that survived the temperature selection.

Figure 2:
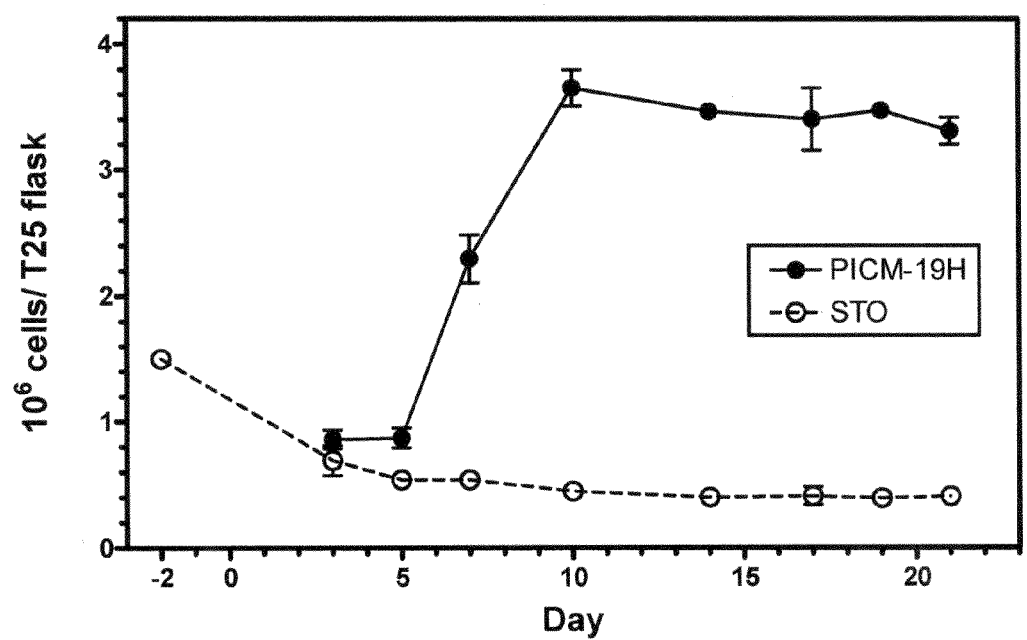
FIG. 2 depicts the PICM-19H growth curve at passage 66 from a 1:6 split ratio passage.

After expansion to mass cultures, by culturing at 37-38° C., it was observed that the PICM-19H cell line did not self-organize into multi-cellular bile ductules under standard or elevated pH culture conditions as is characteristic of the parental ARS-PICM-19 population (FIGS. 1A and B; Talbot et al. 2002, supra). Phase-contrast microscopy showed the PICM-19H cells to be generally cuboidal cells with distinct, centrally located nuclei (FIG. 1B). Like the parental ARS-PICM-19 cells, the fetal hepatocyte-like PICM-19H cells grew as a patch work of small monolayer colonies nestled in amongst the STO (mouse embryonic fibroblast cell line) feeder cells, but, unlike the parental cells that could only achieve approximately 50% confluency, the PICM-19H cells reached approximately 85% confluency before terminal differentiation and contact inhibition markedly slowed their growth (FIG. 1B and FIG. 2).

It was necessary to passage the PICM-19H cultures at least every two weeks in order to keep the majority of the culture's cell cycling, as is the case with parental ARS-PICM-19 cells. The PICM-19H subpopulation was passaged over several years, at 1:3 to 1:10 split ratios, to the current passage level of approximately P175. The PICM-19H cells were cryopreserved at various times over their passage history.

Example 3

Establishment of PICM-19B Stem Cell Line

Figure 3:
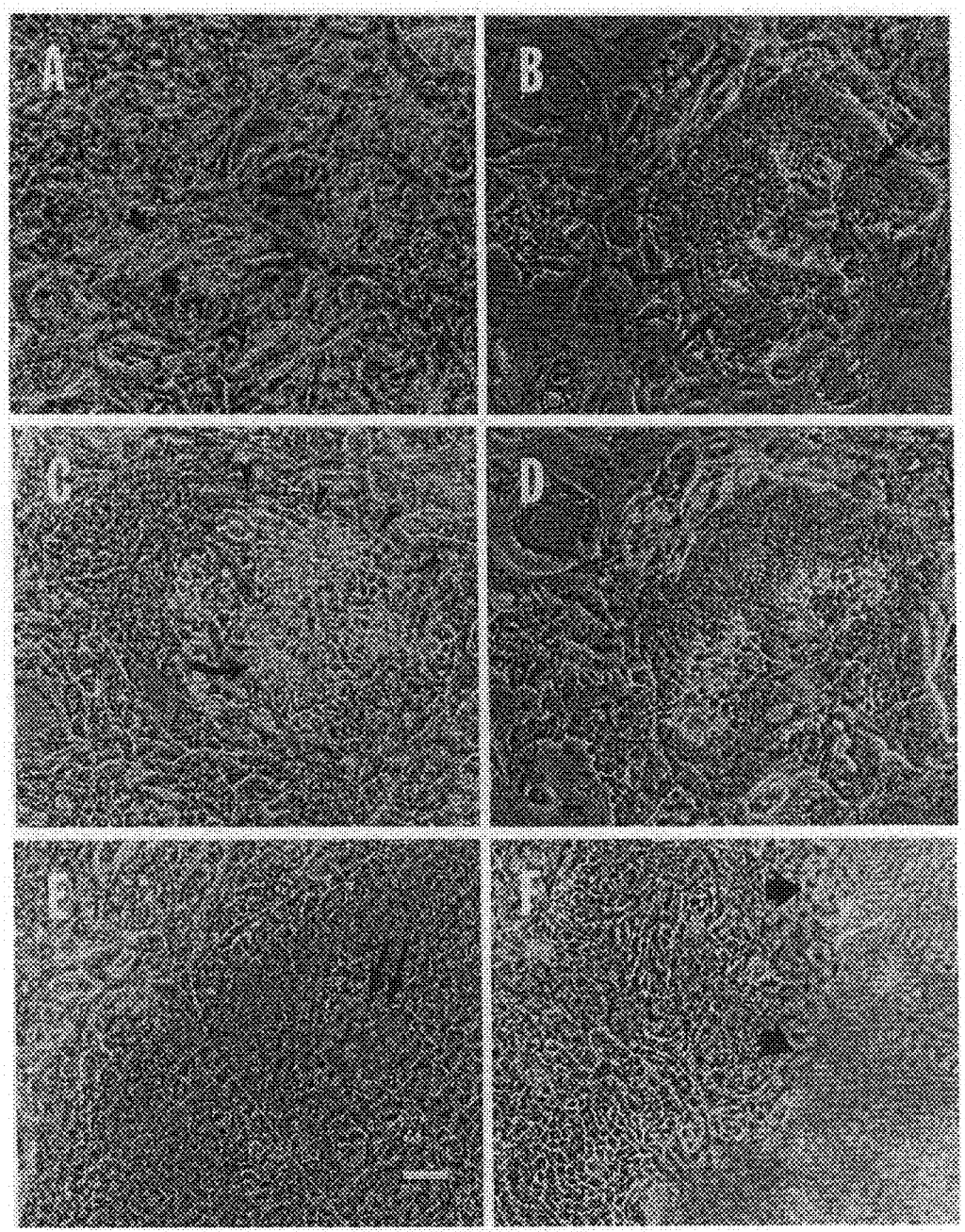
FIGS. 3A-F show phase-contrast micrographs (200×) of an independent PICM liver stem cell line (B, D and F) and the parental ARS-PICM-19 (A, C and E) pig liver stem cell line undergoing phenotypic conversion to dome-forming epithelial cells. The primary event is depicted in A to C and B to D. Note the PICM cells symmetrically arranged in a densely packed columnar morphology along a line of axis (arrows in B) that is a lumenal space between the cells. The lumenal space is filled with a dark material that in A has a yellow color (arrows). Panels C and D depict early expansions with a curved arrow indicating early dome-formation and arrowheads mark the edge of a colonial expansion in C. In Panel E, the PICM-19B cells have flattened and spread, and a small dome is beginning (double arrows). In Panel F the PICM variant cells have multiplied extensively, are flattening out, and a large dome has occurred in the monolayer (arrows). Bar ~50 μm.

The PICM-19B cell line was developed from a spontaneously arising morphological variant of the parental PICM-19 cells which occurred in the culture at low frequency at approximately passage 35 (FIG. 3; Talbot et al. 1994a, supra). The PICM-19B cell line was established by micropipette-mediated colony-cloning of a single colony of this variant cell type. Independent, spontaneously forming, "PICM-19B-like" outgrowths occurred at various passage levels of the parental PICM-19 cells when initiated from frozen stocks of the cells. Observation of the occurrence of the PICM-19B cells, and of many similar independent occurrences, indicated that this morphological variant appeared to arise from PICM-19 cells that were differentiating and forming into bile ductules and not from PICM-19 cells forming monolayer patches of hepatocyte-like cells (Talbot et al. 1994a, supra). To illustrate this point more clearly, FIGS. 3B, C, and D illustrates the genesis of this variant from another independent, epiblast-derived pig liver cell line.

Figure 8:
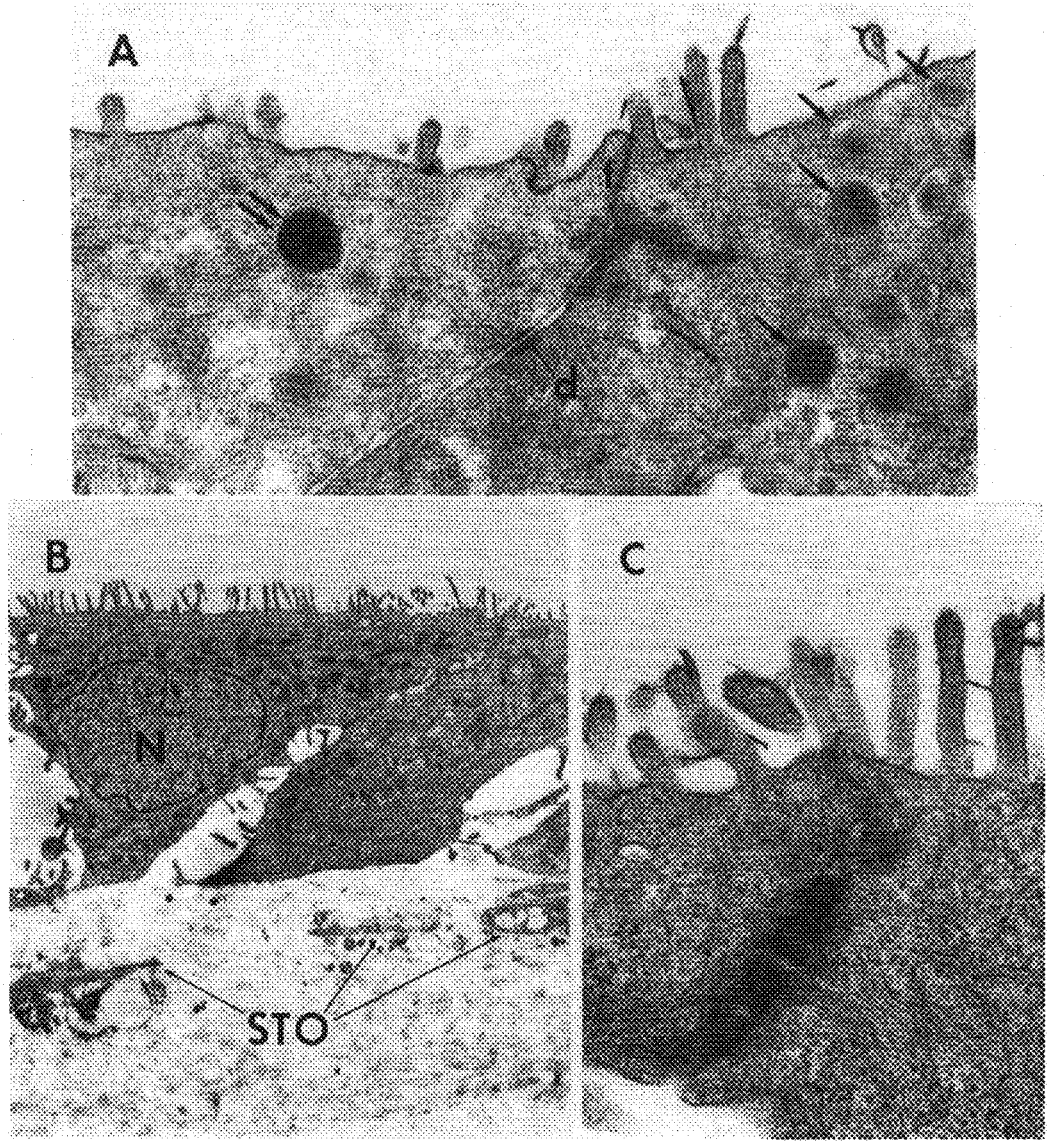
FIG. 8A shows a transmission electron micrograph of PICM-19B-like cells with FIG. 8A showing the apical (facing the culture medium) surface of two cells joined by a tight junction (t) and an associated desmosome-like junction (d). Also, note in FIG. 8A the secretory vesicles (arrows) just below the apical membrane which are typical of mucin containing vesicles with their eccentrically located condensed spherule (double arrows)(magnification: 48,000×).
FIG. 8B shows two PICM-19B cells growing on top of the STO feeder layer and its matrix of collagen fibers. Note the microvilli at the cells apical membrane, the interdigitations of the lateral cell membranes and the typical indented or singularly crenulated nuclei (magnification: 6,000×).
FIG. 8C shows that adhesion belt type junctions can become robust between the cells particularly in areas of the monolayer where domes form through the transport and accumulation of fluid under their basal membrane (magnification: 60,000×).

The occurrence of the "19B" phenotype could first be recognized within the parental PICM-19 culture as colonies of cells that appeared as closely packed and mounded up columnar cells symmetrically arranged around a central point or line (FIGS. 3A and B). The central point or line was a 3-dimensional space that was usually filled with a material that often had a yellowish color under phase-contrast microscopic observation (FIG. 3A). As the cells continued their outgrowth over several weeks, they formed a monolayer of cells that grew over the top of the STO feeder cells or "bulldozed" the feeder cells at the colony's periphery as the colony expanded (FIGS. 3C and D). Unlike the parental ARS-PICM-19 hepatocyte-like monolayers, the 19B variant cell monolayer did not have canalicular connections between its cells. Instead, PICM-19B cells were joined by tight-junctions and displayed apical/basolateral morphological polarity (FIG. 8). The monolayer frequently developed domes (FIGS. 3E and F) indicating apical to basal fluid transport. Also, in some areas of the 19B variant cell monolayers, particularly where domes were present, the cell-to-cell unions had a typical "prickle cell" morphology (FIG. 3F) similar to skin epithelium where robust desmosomal connections join adjacent cells (Alberts et al. 1994. Molecular Biology of the Cell, Second Edition, Garland Publishing, New York, Pages 789 and 954-955).

Figure 4:
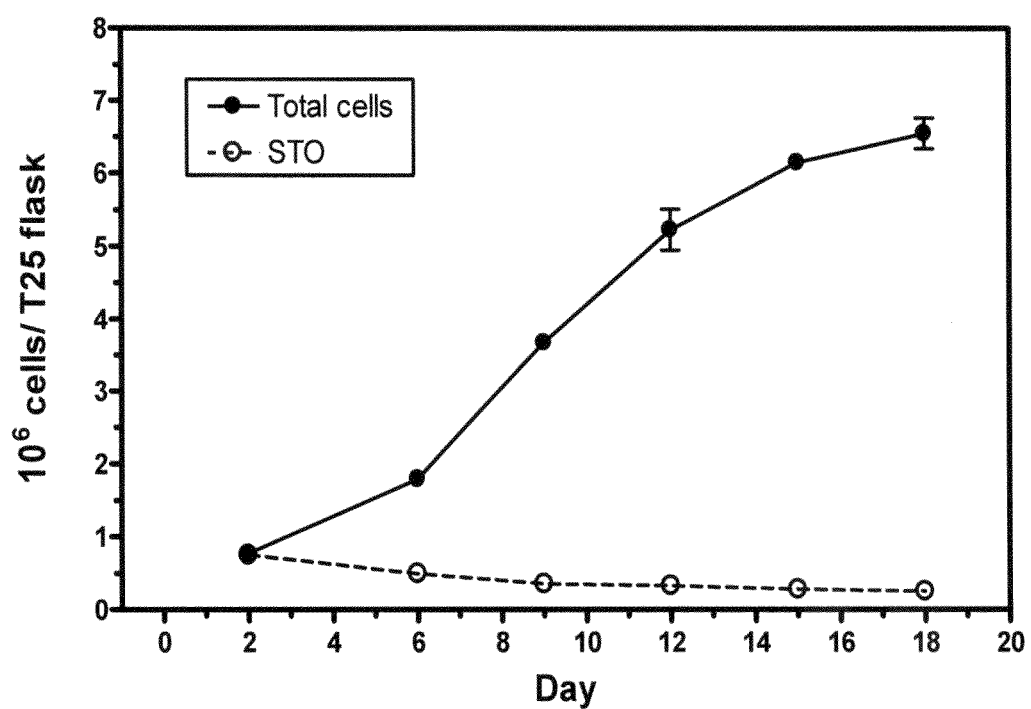
FIG. 4 depicts the PICM-19B growth curve at passage 64 from a 1:12 split ratio passage.

In contrast to the terminally differentiating and self-organizing bile ductule cells of the parental ARS-PICM-19 cell line, the 19B variant cells grew to 100% confluency which resulted in a final cell density of approximately $2.61 \times 10^5$ cells/cm$^2$ (FIG. 4). The parental ARS-PICM-19 cells have never achieved more than 60-75% confluency before terminally differentiating (Talbot et al. 1994a, 2002 supra). Also, despite their basolaterally polarized monolayer characteristic, the 19B variant cells were found to be more easily dissociated from one another after trypsin-EDTA treatment than the parental ARS-PICM-19 cells. The PICM-19B cell line was passaged at 1:5 to 1:10 split ratios until the 89$^{th}$ passage, a time period of greater than one year. The PICM-19B cells were cryopreserved at various times over their passage history.

Example 4

Cell Growth Assays

PICM-19H and PICM-19B cell growth was assayed at passage 66 and 64, respectively, by counting the increase in the total cells per T25 flask over a 3 wk period at 2-4-day intervals post-passage. Duplicate T25 flasks were counted at each time interval. Single cell suspensions of the contents of each flask were produced by trypsin-EDTA dissociation. The cells were suspended to a total volume of 2 ml in 10% DMEM for cell counts. The total number of cells per T25 flask was determined by averaging the counts of 16 hemocytometer squares (1 mm$^2$). Input of the number of PICM-19H and PICM-19B cells at the start of the growth assay was undefined, but was a 1:6 split ratio for PICM-19H and a 1:12 split ratio for PICM-19B, each from nearly confluent stock cultures. STO feeder-cells surviving the trypsin/EDTA dissociation were similarly enumerated from a parallel group of feeder-cell T25 flasks that had not received any PICM cell input.

The growth curve of the PICM-19H cells indicated a lag period of 3-5 days post-passage, a logarithmic growth phase with a doubling time of approximately 48 h and a differentiation driven plateau phase where the final cell number reached per T25 flask was nearly 4 million cells or approximately 1.49×10$^5$ cells/cm$^2$ (FIG. 2).

The PICM-19B variant cells grew to 100% confluency which resulted in a final cell density of approximately 2.61× 10$^5$ cells/cm$^2$. The 19B's doubling time during logarithmic growth was approximately 48-72 h (FIG. 4).

Example 5

Ultrastructure Analysis

Transmission Electron Microscopy

Transmission electron microscopy (TEM) sample preparation and photomicroscopy were done with the assistance of JFE Enterprises, Brookeville, Md. as previously described (Talbot et al. 1998, supra; Talbot et al. 2000. *Tissue and Cell* 32: 9-27). Ultrastructural analysis was performed on samples processed from T25 flask cultures that were 6-wk post-passage for PICM-19H and 8-wk post-passage for PICM-19B-like cells that had spontaneously formed within the parental ARS-PICM-19 culture.

Figure 5:
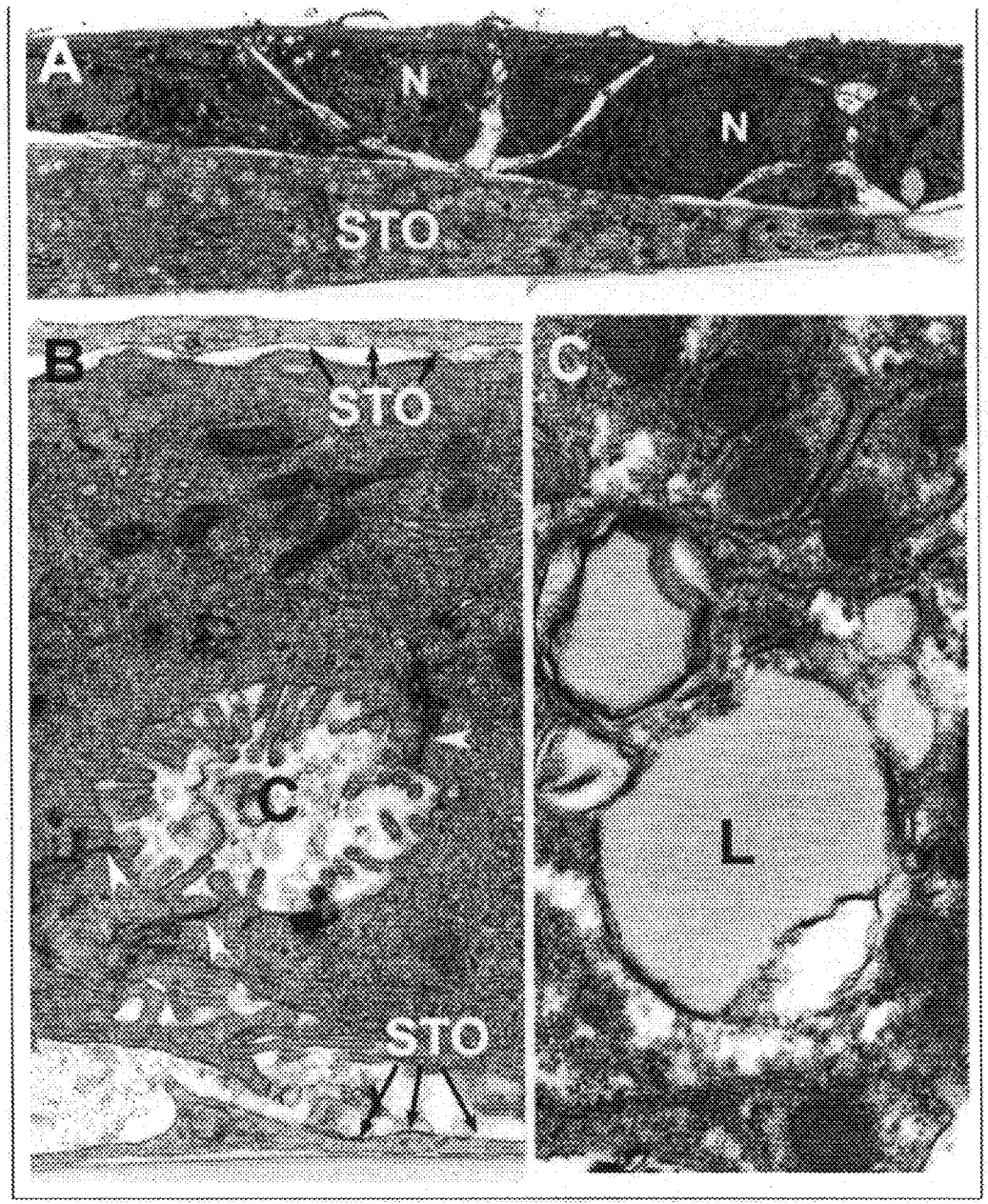
FIG. 5A shows a transmission electron micrograph of PICM-19H cells arranged in a monolayer situated on top of a large STO feeder cell at 6000× magnification.
FIG. 5B shows a biliary canaliculi (c) occurring between the PICM-19H cells with associated tight junctions (arrowheads). Also, note the STO feeder cells are both above and below the PICM-19H cells (magnification 33,800×).
FIG. 5C shows that some lipid vacuoles (L) were found in PICM-19H cells (magnification: 60,000×).

The ultrastructure features of the PICM-19H cells are similar to those observed in the hepatocyte-like cells of the parental ARS-PICM-19 cultures (Talbot et al. 1996a, supra). The ultrastructural feature perhaps most defining of hepatocytes is the specialized cell-to-cell union that occurs between hepatocytes to form a biliary canaliculus (Wanson et al. 1977. *J. Cell Biol.* 74: 858-877). PICM-19H cells are closely associated with one another by extensive plasma membrane foldings that are interdigitated along their lateral surfaces (FIG. 5A) and are often are found sandwiched between STO feeder cells (FIG. 5B). Junctional apparati typical of polarized epithelial cells are found between adjacent PICM-19H cells at their lateral apical surfaces, i.e., facing the lumen of the biliary canalicular spaces (FIG. 5B). These tight-junction-like unions establish the impermeable boundaries of the biliary canaliculi that exist between adjacent PICM-19H cells as has been previously shown by ruthenium red staining (Talbot et al. 1996a, supra). The biliary canalicular surface has numerous microvilli that protrude into the canalicular space (FIG. 5B).

The biliary canaliculi formed by PICM-19H are similar to those found in vivo in thin sections of human embryonic, piglet, and rodent liver (Enzan et al. 1974. *Acta Pathol. Jap.* 24: 427-447; Singh and Shahidi. 1987. Ultrastructure of Piglet Liver In: *Swine in Biomedical Research*, M E. Tumbleson (Ed), Volume 1, Plenum Press, New York, page 84; Wanson et al., supra), and, as with the parental cells, are responsive to added secretin or glucagon, i.e., they display transcellular movement of fluid into the canaliculus (not shown; Talbot et al. 2002, supra).

Figure 6:
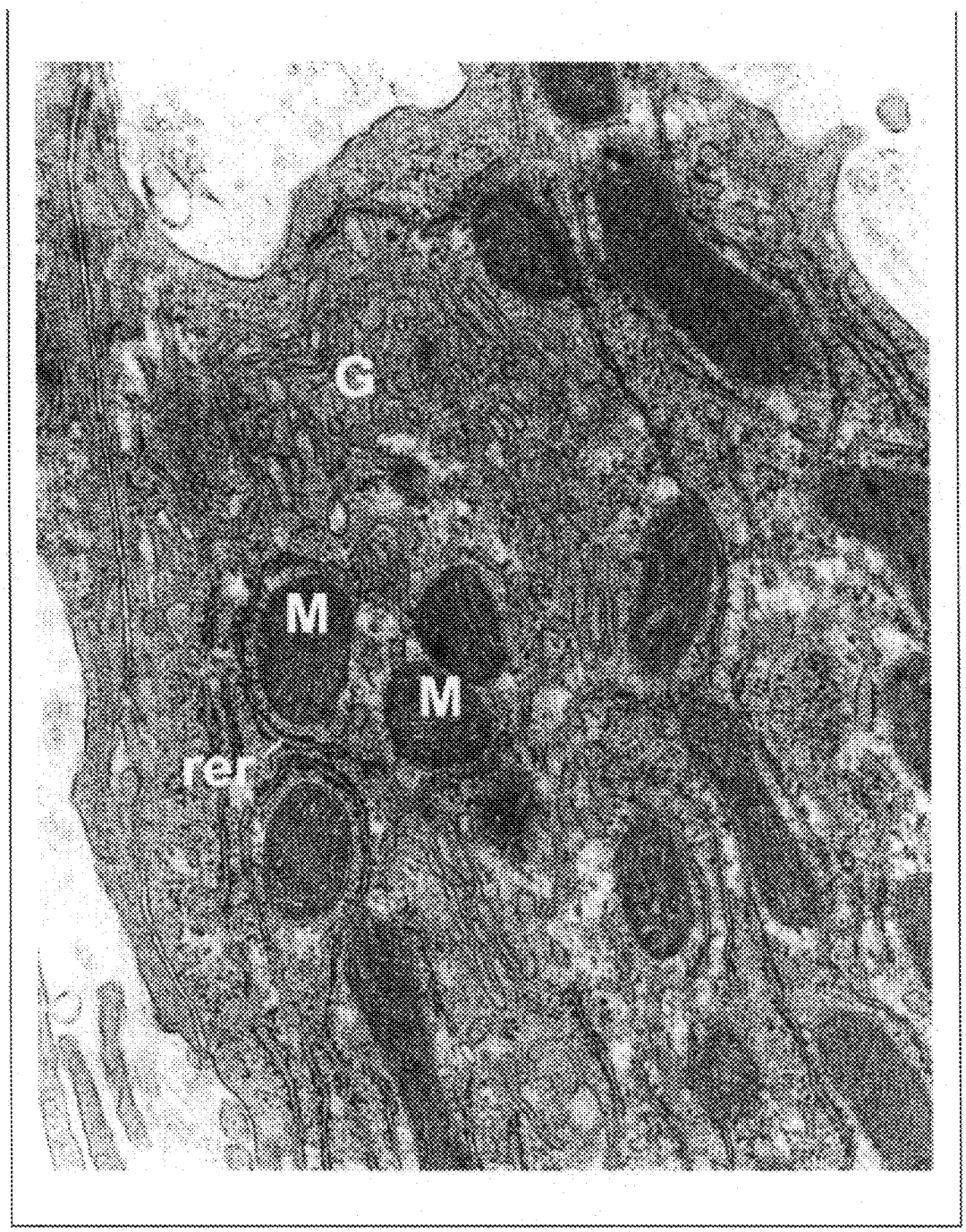
FIG. 6 shows a transmission electron micrograph of PICM-19H cells highlighting the extensive Golgi complexes (G), rough endoplasmic reticulum (RER), and numerous mitochondria (M) found within the cells (magnification: 60,000×).

The nuclei of the cells are oval and often display a single deep invagination (FIG. 5A). Rough endoplasmic reticulum (RER) is particularly well represented in the cells and is often found in extensive stacks that surround some of the mitochondria of the cells (FIG. 6). However, the RER cisternae are relatively collapsed indicating that they contain relatively little secretory material. While other PICM-19H and PICM-19B ultrastructural features are typical of hepatocytes or bile duct epithelium, the extensive RER arranged in long laminar cisternae found in both cell lines is not. This feature is most like that reported in hepatoblasts of human fetal liver where extensive multi-zonal collections of RER with long cisternae are present. In contrast, fetal and adult bile duct epithelium cells are found to have very little and short tubular RER (Enzan et al. 1974. *Acta Pathol. Jap.* 24: 427-447.; Ishii et al. 1989. *Physiol. Rev.* 69: 708-764; Phillips et al. 1987. In: *The Liver An Atlas and Text of Ultrastructural Pathology*, Phillips et al., Eds., Raven Press, New York, pp. 1-35. This distinction is not apparent in comparing PICM-19H and PICM-19B cells, and, therefore, like the parental ARS-PICM-19 cells, it may indicate that the derivative cell lines are either fundamentally different from in vivo fetal liver cells because of the in vitro environment, or that they still display a transitional morphology similar to hepatoblasts that can "mature" given the proper environment.

Figure 7:
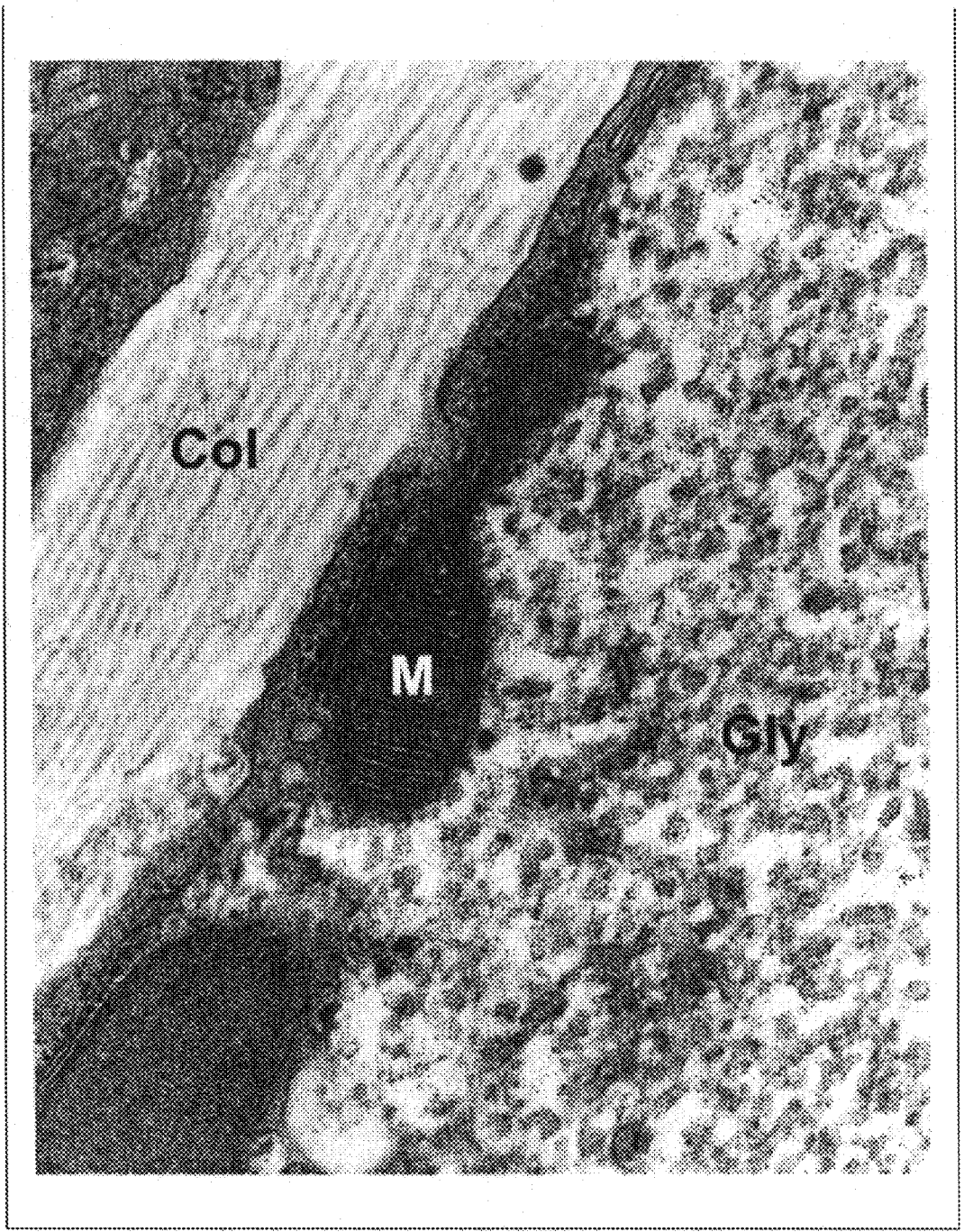
FIG. 7 shows a transmission electron micrograph of PICM-19H cell showing what appeared to be remnants of poorly fixed areas of glycogen rosettes (GLY). Also, note the layer of collagen fibrils (Col), presumably produced by the adjacent STO feeder cell, and the lamellar cristae characteristically traversing the PICM-19H cell's mitochondrion (M) (magnification: 94,500×).

Smooth ER also appears to be present in the cells, but it is difficult to discriminate from Golgi complexes with certainty. Golgi complexes which are often found in a supranuclear position are well developed and numerous (FIG. 6). Mitochondria are elongate (2-3 μm in length) in longitudinal section and oval (0.2-0.3 μm in diameter) in cross-section (FIG. 6). Their lamellar cristae characteristically traverse the mitochondrion and electron dense granules are sometimes present within their matrixes. Numerous-peroxisome-like organelles are also present throughout the cell's cytoplasm although their identification as peroxisomes is not proven. Relatively "empty" areas of cytoplasm with residual glycogen-like granules in them are frequently observed in the PICM-19H cells (FIG. 7). Presumably these are areas of glycogen storage that are mostly lost as a result of inadequate glycogen rosette fixation. Finally, no monocilia are observed in the PICM-19H cells examined.

Figure 9:
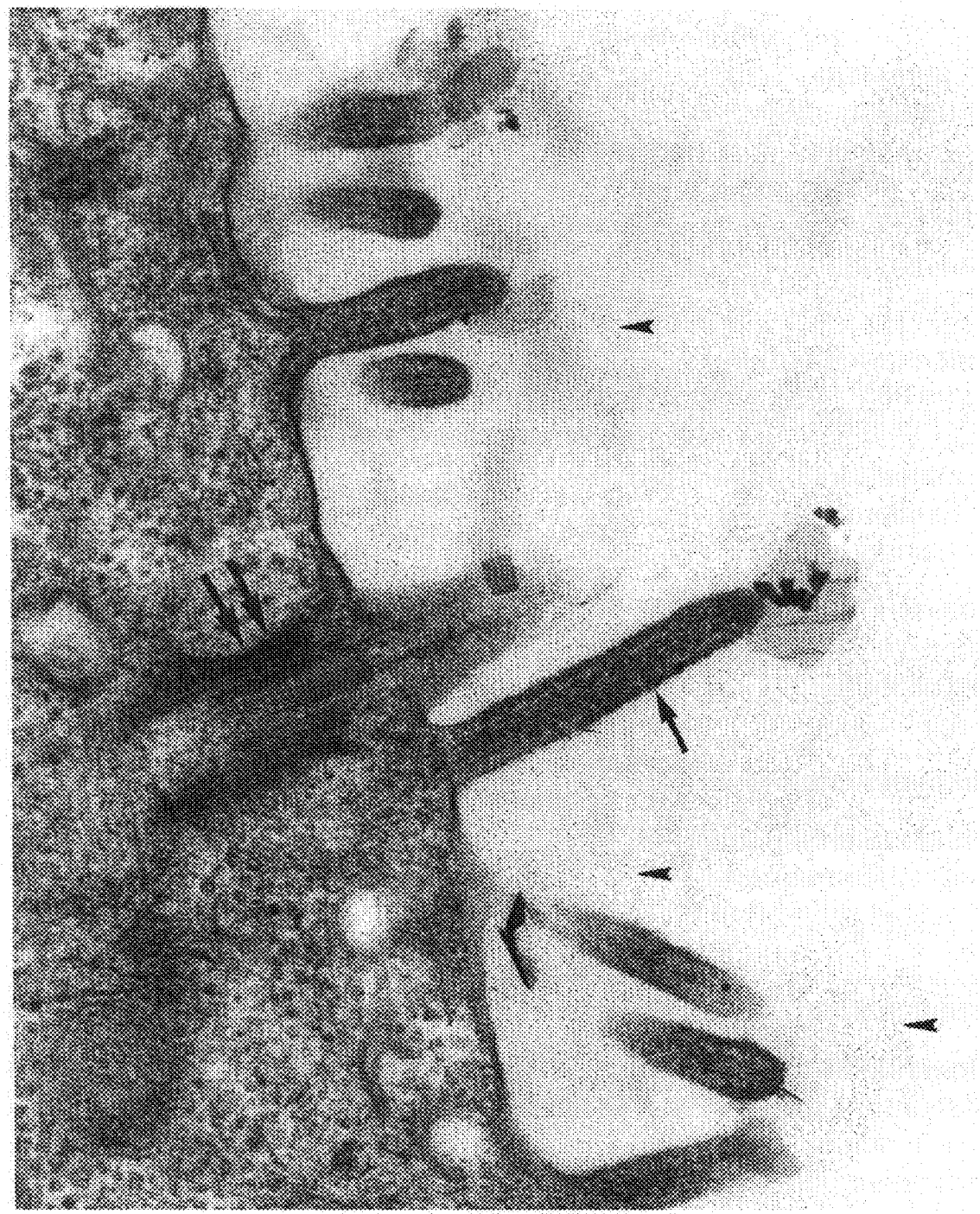
FIG. 9 shows a transmission electron micrograph of PICM-19B-like cells. Apical surface of cells with microvilli (arrow) and cilium basal body (double arrows). Note the staining of the glycocalyx, which also held precipitated stain (arrowheads) (magnification: 120,000×).

The ultrastructure of PICM-19B cells show features more typical of hepatic biliary epithelium (cholangiocytes) or gallbladder epithelium. In contrast to PICM-19H cells, PICM-19B cells form a monolayer of interdigitating cells with a clear basal/apical polarization, but without canalicular formations, i.e., the cells are arranged in a continuous epithelial sheet with tight junctions, as evidenced by dome-formation (FIGS. 1 and 8B). Microvilli of a moderate, uniform height (0.4-0.6 μm) are found on the apical surfaces of the cells (FIGS. 8A and 8C). The microvilli have particularly distinct internal actin filaments that run deep into the underlying cytoplasm before joining the adhesion-belt actin filaments that run parallel to the apical cytoplasmic surface. Tight junctional elements and desmosomes join the cells together at their apical and lateral unions, and interdigiting cytoplasmic foldings are also common at lateral cell surfaces (FIGS. 8A and 8C). The cells also have numerous and well developed perinuclear Golgi apparatus, and secretory vesicles are frequently observed in the cytoplasm between the nucleus and apical cell membrane (FIGS. 9 and 8A). The contents of the secretory vesicles are usually similar to or darker in electron density than that of the surrounding cytoplasm and, as is typical of the muscin containing vesicles of gallbladder epithelium (Gilloteaux et al. 1997. *Microsc. Res. Tech.* 38: 643-659), they often contain an eccentrically located dense spherule (FIG. 8A). The cells display cilia, although infrequently, and therefore, the cells are probably monociliated (FIG. 9).

Cilia are not observed by electron microscopy in the PICM-19H ultrathin sections, but are observed, mostly likely as monocilia on the apical surface of the PICM-19B cells. Cilia have not been found in human hepatoblasts or piglet hepatocytes (Enzan et al., supra; Singh and Shahidi, supra). In contrast, the presence of monocilia was shown to be a characteristic feature of fetal human, neonatal pig, and adult rat bile duct epithelium cells (Enzan et al., supra; Ishii et al., supra; Singh and Shahidi, supra) or gallbladder epithelium cells (Nakanuma et al. 1997. *Microsc. Res. Tech.* 39: 71-84). Therefore, the absence and presence of monocilia on PICM-19H cells and PICM-19B cells, respectively, is consistent with the PICM-19H cells being more hepatocyte-like in phenotype and the PICM-19B cells being more bile duct- or gallbladder-epithelium-like.

Figure 10:
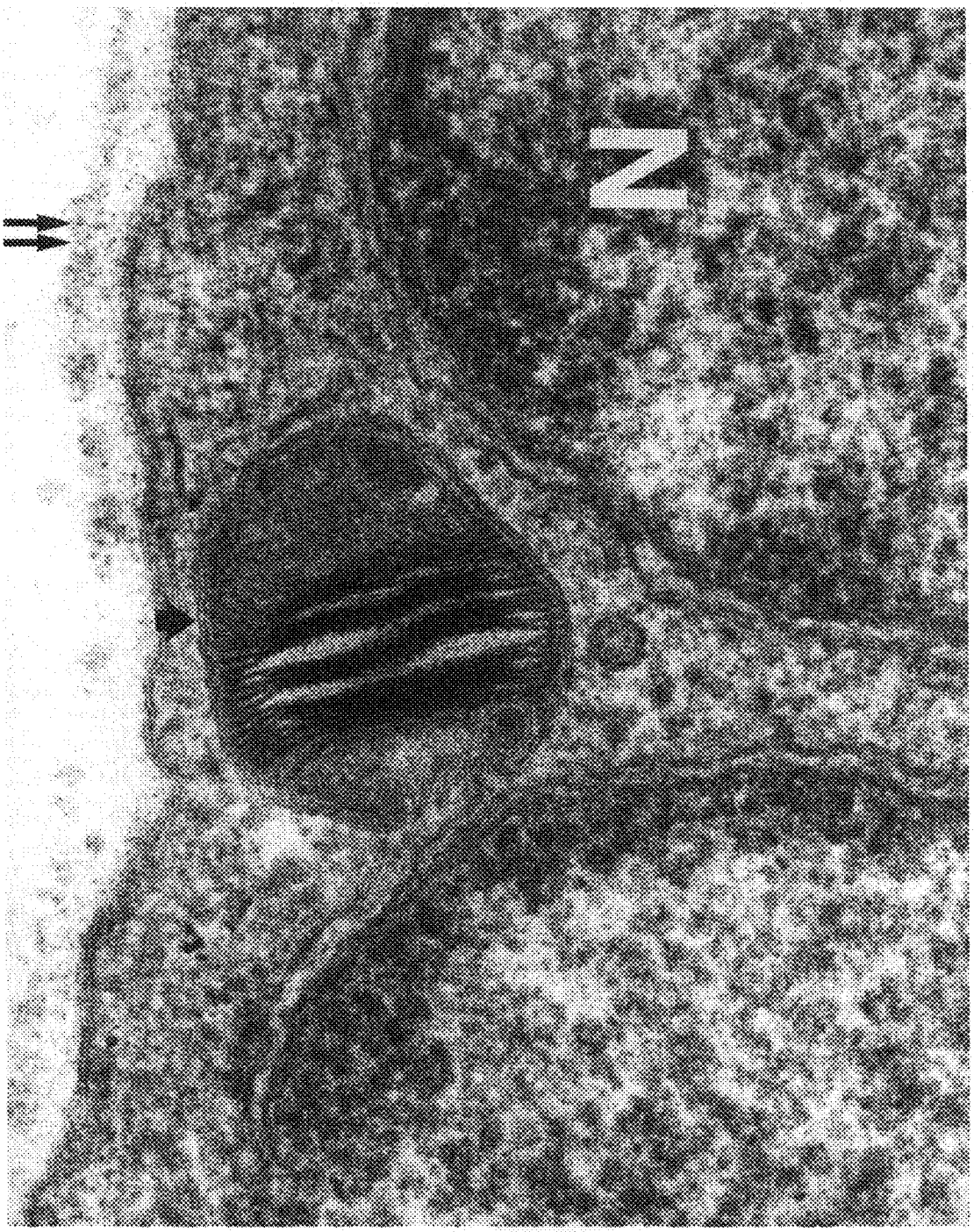
FIG. 10 shows a transmission electron micrograph of the basal aspect of a PICM-19B-like cell showing a microbody (arrow) containing numerous parallel prismatic plates. The microbody appears to have a double membrane like a mitochondrion. The crystalloid array may be the nucleoid of a peroxisome or perhaps a condensation within a lysosome. Note the sparse basal lamina below the bottom of the cells (double arrows)(N=nucleus; magnification: 240,000×).
Figure 11:
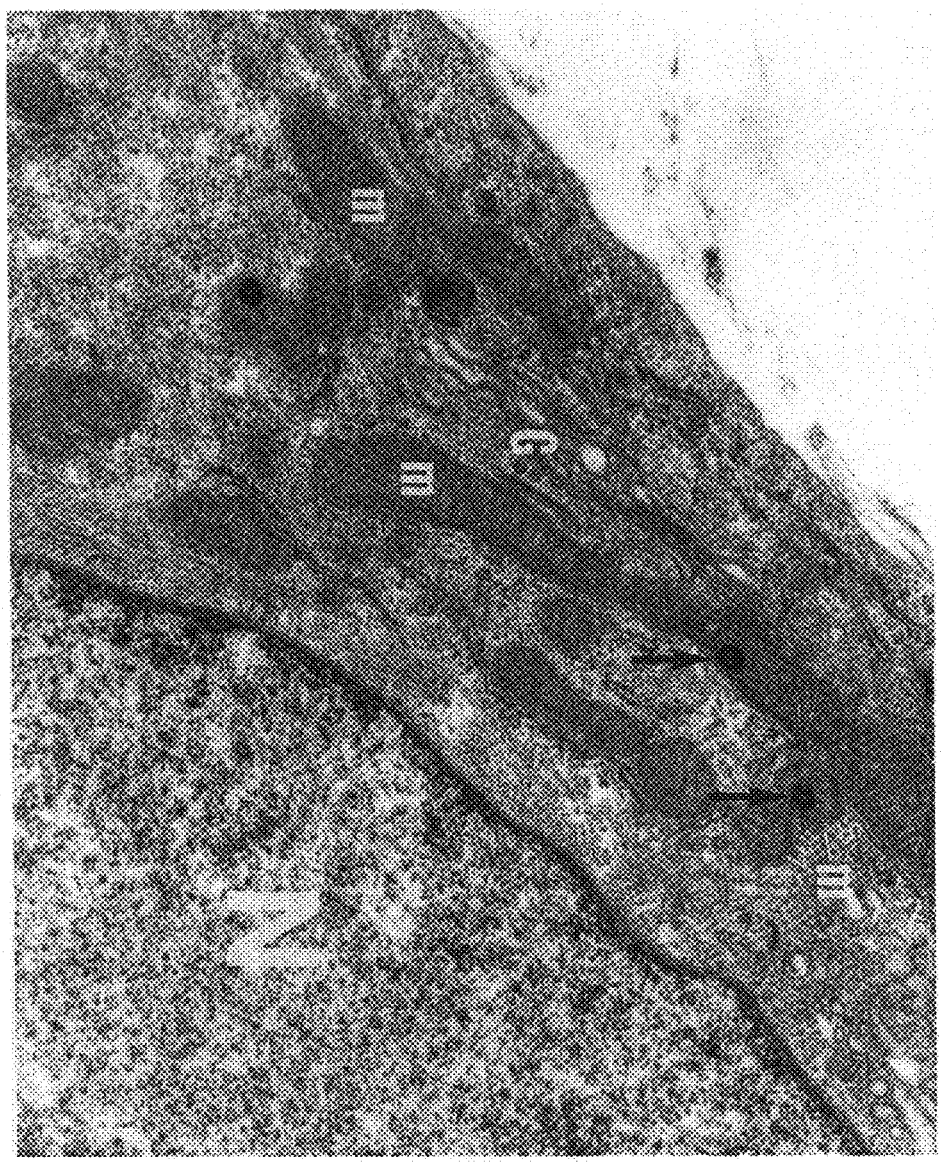
FIG. 11 shows a transmission electron micrograph of PICM-19B-like cells. Note the long mitochondria with matrix granules (arrows) and the well developed Golgi apparatus (G) that were frequently seen around the nucleus (N) (magnification: 48,000×).

Membrane-bound bodies resembling peroxisomes are numerous in PICM-19B cells and some have prismatic parallel plate-like structures in their interior (FIG. 10). Also, mitochondria with lamellar cristae are numerous and are sometimes found to contain one or more granules, apparently distributed randomly in their matrix (FIG. 11). Both smooth and rough endoplasmic reticulum (RER) are found in the cells, although the former is difficult to distinguish from the many Golgi complexes present (FIG. 11). The RER sometimes occurs in extensive stacks, although their cisternae are relatively collapsed, indicating that they contained relatively little secretory material. As found in PICM-19H cultures, a matrix of collagen fibrils is evident between the STO feeder cells and the PICM-19B cells, presumably having been produced by the STO fibroblasts. However, in contrast with the PICM-19H culture, the STO feeder cells are mostly situated underneath the PICM-19B cell monolayer (FIG. 8B). Finally, a thin basal lamina can be discerned below the basal membrane of the PICM-19B cells (FIG. 10).

Example 6

Assay of γ-Glutamyltranspeptidase (GGT) Activity and CYP450 Content

T25 cultures of PICM-19H and PICM-19B cells were grown for approximately 3 wk post-passage and the cultures were scraped and harvested for whole cell homogenates and microsomes. Two days prior to harvest the cultures were exposed to metyrapone to stimulate CYP450 expression. CYP450 content and GGT activity were determined as previously described (Talbot et al. 1996, supra) from a pool of three flasks.

CYP450 is present in the microsomal fraction of PICM-19H and PICM-19B cells that had been exposed to metyrapone for 48 h prior to assay (Table 1). In contrast, CYP450 is undetectable in PICM-19 cell culture homogenates that had not been exposed to metyrapone (data not shown). The crude homogenate and microsomal fraction of STO feeder cells grown under identical conditions and treated with metyrapone have no detectable CYP450 content. Because the microsomal protein associated with STO cells represent more than one-third of the total harvested microsomal protein, the actual specific content of CYP450 (nmoles/mg/protein) in the PICM-19H and PICM-19B cells is greater than reported. PICM-19B CYP450 content was also compared to freshly harvested pig hepatocytes (Table 1) and the results show the cell line to contain approximately one-sixth the CYP450 of freshly harvested adult pig hepatocytes.

Figure 12:
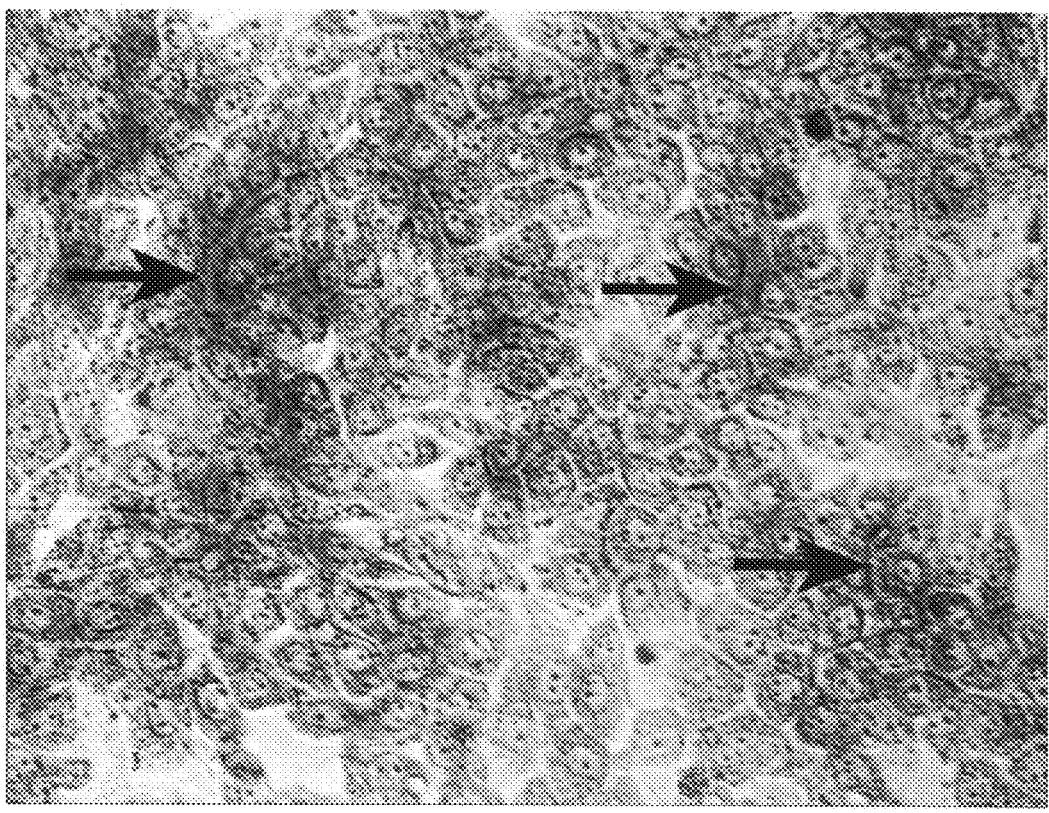
FIG. 12 shows a phase-contrast photomicrograph of PICM-19H cell monolayer histochemically stained for GGT activity. Arrows denote biliary canaliculi between PICM-19H cells showing positive staining (red color) for GGT activity.
Figure 13:
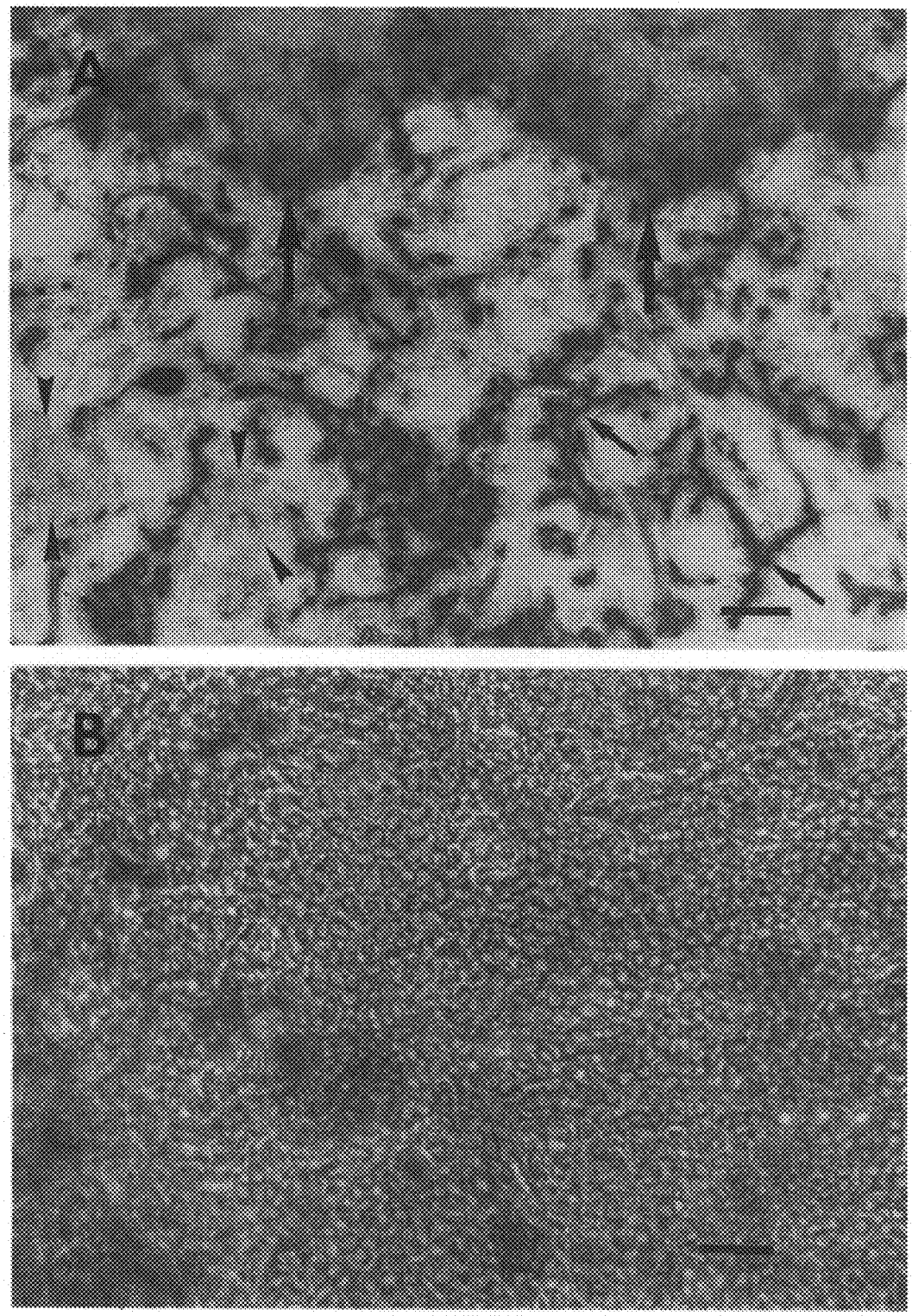
FIG. 13 shows bright field (FIG. 13A) and phase-contrast (FIG. 13B) photomicrographs of parental ARS-PICM-19 liver stem cell cultures histochemically stained for GGT activity.

GGT activity is found in both PICM-19H and PICM-19B cells by histochemical staining. PICM-19H GGT activity is specifically expressed at the biliary canaliculi visible in PICM-19H monolayers (FIG. 12), whereas in PICM-19B cells the GGT staining is diffuse and is associated with all of the cells (FIG. 13). GGT activity was also measured in the homogenates of PICM-19H and -19B cells cultured for three to four weeks (Table 1). Total GGT activity was markedly higher in PICM-19B cells compared to that found in the homogenates of freshly harvested pig hepatocytes or PICM-19H cells (Table 1). The STO feeder cell homogenates show very low or no GGT activity when grown alone under the same conditions as the PICM-19 cells (not reported). The reported specific activity of GGT in PICM-19, total GGT, is therefore underestimated because approximately two-fifths of the cell culture homogenate protein is derived from the STO feeder cells. PICM-19B cells had 84 times as much GGT activity as the freshly harvested pig hepatocyte preparation. PICM-19B cells had approximately 6 times more GGT activity than PICM-19H cells (Table 1).

TABLE 1

Levels of CYP450 and activity of GGT in PICM-19H, PICM-19B, and Adult Porcine Hepatocytes.

| Cell Type | CYP450 (pmoles/mg microsomal protein) | GGT (m units/mg protein) |
|---|---|---|
| PICM-19H | *136 ± 35 (n = 3) | 51.2 ± 1.7 (n = 9) |
| PICM-19B | *#BD (n = 2) | 311.9 ± 9.4 (n = 9) |
| Adult Porcine Hepatocytes (freshly prepared) | 617 ± 47 (n = 4) | 3.7 ± 0.4 (n = 4) |

*48 hr post metyrapone addition
BD: Below Detection

GGT is highly expressed in bile duct epithelium and thought to be a good marker for this cell type (Tanaka, M. 1974. *Acta. Path. Jpn.* 24: 651-665; Ishii et al., supra). Previously the parental ARS-PICM-19 cells were demonstrated by histochemical staining to have GGT activity localized to the plasma membranes of their biliary canaliculi as has been found in primary hepatocyte cultures (Meister et al. 1976. In: *The Enzymes of Biological Membranes*, Martinosi, A. (Ed.), Plenum, New York, pages 315-347; Talbot et al. 1996a; supra). As shown here, PICM-19H cells have a similar expression pattern (FIG. 12).

In comparison, the PICM-19B cells have a more robust GGT expression (Table 1) and, when viewed microscopically, a seemingly ubiquitous GGT expression. This overall cell-surface histochemical GGT staining probably results from the GGT expression being associated with the apical membranes of PICM-19B cells which, in aspect, are parallel with the focal plane of the microscopic image. The majority of PICM-19H cells appear devoid of GGT staining because of the localization to biliary canaliculi, and perhaps it is not localized to all biliary canaliculi, and because the canaliculus constitutes a discrete side-to-side polarization within the PICM-19H monolayer. This polar distribution of GGT is indicative of the transport function of the enzyme in the specialized apical areas of hepatocytes and cholangiocytes (Meister et al., supra). The enhanced GGT expression of PICM-19B, and conversely the relatively low expression found in PICM-19H, are again indicative of a more bile duct-like or gallbladder epithelium-like phenotype for the PICM-19B cells and a more hepatocyte-like phenotype for the PICM-19H cells.

Example 7

CYP450 EROD Activity Assay

Figure 14:
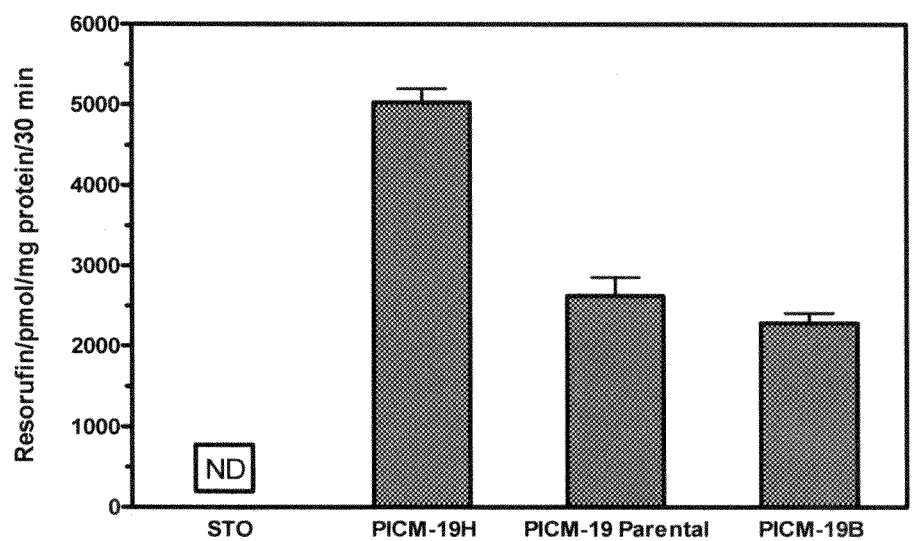
FIG. 14 depicts 3-methylcholanthrene-induced CYP450 activity in PICM-19 cell lines as measured by EROD assay. Un-induced CYP450 values were below the limit of detection and are not shown. ND=not detectable.

Three nearly confluent T25 flask cultures of PICM-19H and PICM-19B cells were pre-incubated with 5 μM 3-methylcholanthrene (3-MC) in culture medium for 48 h to induce CYPA1 activity. 3-MC-induced CYP450 activity was measured by EROD assay, i.e., by conversion of 7-ethoxyresorufin (7-ERF) to the highly fluorescent product resorufin, in PICM-19H cells, PICM-19B cells, parental ARS-PICM-19 cells, and in STO feeder cells alone (FIG. 14). Cells were exposed to Medium 199 medium with Hank's salts without L-glutamine or sodium bicarbonate and containing 7-ERF (8 μM), dicumerol (10 μM), and bovine serum albumin for 30 min as described by Donato and coworkers (1993. *Anal. Biochem.* 213: 29-33). The medium was harvested and the concentration of the fluorescent product, resorufin, was assayed in the presence and absence of β-glucuronidase/arylsulfatase (Roche Applied Sciences, Mannhein, Germany) to determine the extent of possible conjugation reactions. All reagents were from Sigma-Aldrich (St. Louis, Mo.) and activity is presented as pmole product formed per 30 min/mg cell protein in cultures prepared with and without 3-MC. T25 flasks of STO feeder cells only were also assayed as to control for their presence in the PICM-19 cultures.

PICM-19H cells converted 7-ERF to resorufin at rates of approximately $5 \times 10^3$ pmole per 30 min/mg cell protein. Induced EROD activity is also found in PICM-19B cells, but its levels are comparatively reduced at approximately 50% of that measured in PICM-19H cells. ARS-PICM-19 parental cells have only marginally higher rates of resorufin production than the PICM-19B cells. STO feeder cells show no detectable CYP450 activity. EROD activity is below the level of detection in all of the PICM-19 cell cultures when not induced by exposure to 3-MC (not shown).

PICM-19H cells display higher inducible CYP450 content when exposed to 3-MC for 48 h then do PICM-19B cells and parental ARS-PICM-19 cells. Similarly, CYP450 activity, measured by conversion of 7-ER to resorufin, is also higher in the PICM-19H cells (FIG. 14). The ability to induce relatively high amounts of CYP450 in the PICM-19H cells is consistent with a hepatic phenotype (Murray et al., 1987. *Gastroenterology* 93: 141-147; Brill et al. 1993. *Proc. Soc. Exp. Bio. Med.* 204: 261-269), whereas the lower amounts seen in the PICM-19B cells indicates the cells trending towards a phenotype typical of cholangiocytes (Sirica, A. E. 1992. *Progress in Liver Diseases* 10: 63-87; Alpini et al. 1994. The Biology of Biliary Epithelia. In: *The Liver: Biology and Pathobiology*, Arias et al. (Eds.), Raven Press, New York, pages 623-653; Talbot et al. 1998, supra). In the parental ARS-PICM-19 cell line it was previously suggested that CYP450 levels probably depended upon the relative proportions and extent of the alternative differentiated phenotypes, i.e., the hepatocyte monolayer differentiated cells having more CYP450 activity than the PICM-19 cells that differentiated into bile ductules (Talbot et al. 1996a, supra). Thus, the loss of the bile ductule differentiation phenotype in the PICM-19H cell line can enhance total CYP450 activity of these cultures compared to those of the parental ARS-PICM-19 cell line, cell numbers being equal, since no PICM-19H cells differentiate to form bile ductules which largely lack CYP450 activity relative to hepatocytes (Sirica, supra; Alpini et al., supra; Talbot et al. 1998, supra).

Example 8

Two-Dimensional Electrophoretic Analysis of Conditioned Medium

Mass Spectrophotometric Analysis of Proteins

PICM-19H or PICM-19B cells were seeded into T25 flasks and cultured as previously described (Talbot et al. 1996, supra). At approximately 2 wk post-passage, medium was removed and the flasks were rinsed four times with serum-free DMEM medium, to remove FBS-related proteins, and the flasks were culture 48 h in 4 ml of serum-free DMEM. The conditioned medium (CM) was collected and cell debris was pelleted by centrifugation at ~500×g for 15 min. The proteins of the CM were concentrated and separated by isoelectric focusing as previously described (Talbot et al. 2007. *In Vitro Cell dev. Biol. Anim.* 43: 72-86). Second dimension separations were also done as previously described (Talbot et al. 2007, supra) on 10% polyacrylamide gels (8×10 cm). The proteins in the gel were visualized by staining with Colloidal Coomassie Blue G-250 (Gradipure®; Life Therapeutics, Frenchs Forest, Australia) and the gel was scanned using laser densitometry (PDSI, GE Healthcare). The CM from STO feeder cells alone was similarly analyzed as a control for their presence in the PICM-19 cultures and for FBS-related proteins.

Protein spots were excised from 2D gels using standard pipette tips and the gel "plugs" were processed as previously described (Talbot et al. 2007, supra). A Voyager DE-STR MALDI-TOF mass spectrometer (Applied Biosystems, Framingham, Mass.) operated in positive ion reflector mode was used to analyze tryptic peptides, and spectra were acquired with 75 shots of a 337 nm Nitrogen Laser operating at 20 Hz. Spectra were calibrated using the trypsin autolysis peaks at m/z 842.51 and 2,211.10 as internal standards.

Figure 15:
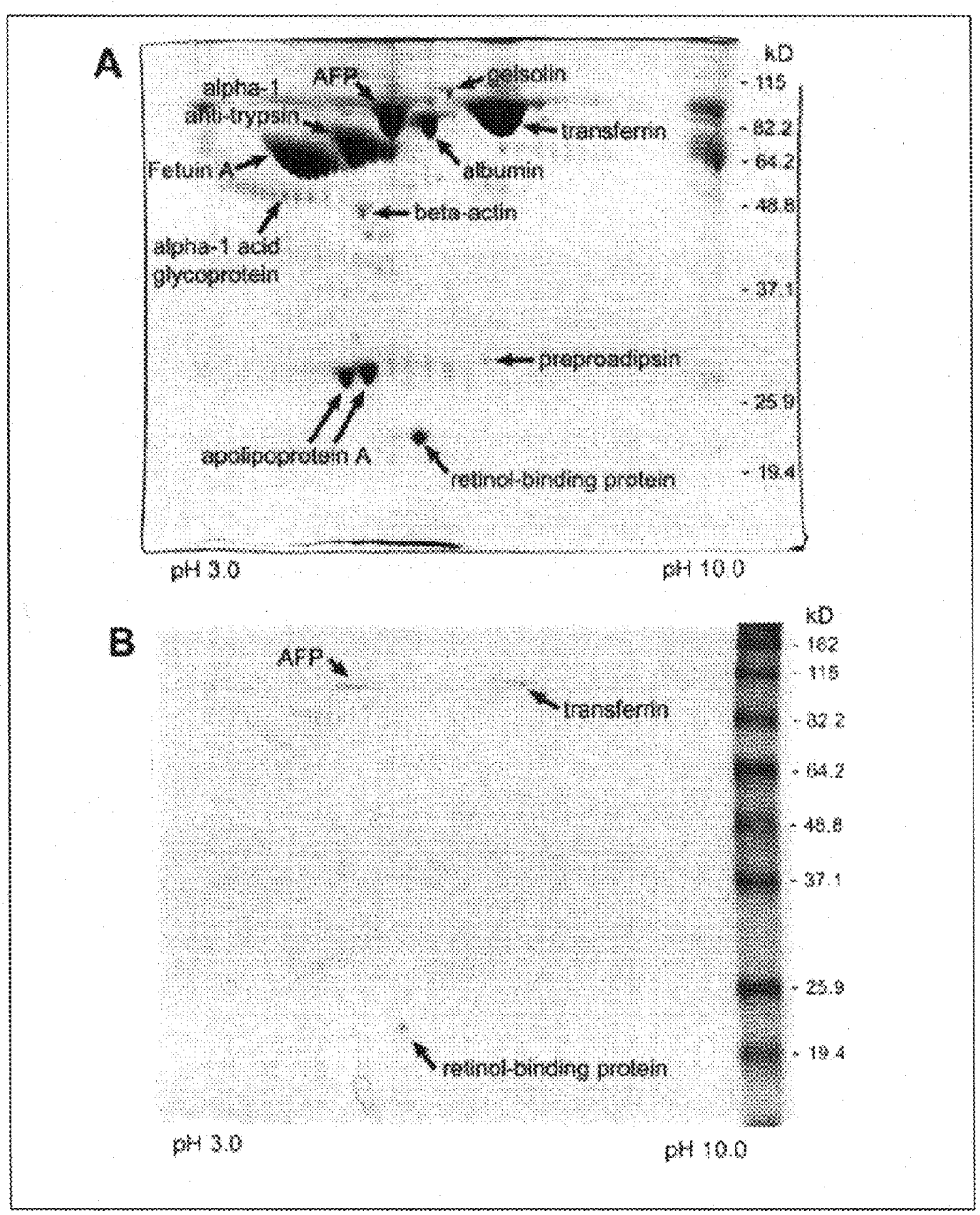
FIG. 15 shows a two-dimensional polyacrylamide gel of serum-free medium samples conditioned for 48 h by nearly confluent monolayers of PICM-19H cells (FIG. 15A) or PICM-19B cells (FIG. 15B). Gels were stained with colloidal Coomassie-Blue and some serum proteins, as identified by MALDI-TOF and LC-MS, are indicated (see also Table 2).

Analysis of serum-free medium conditioned by PICM-19H cells for 48 h showed that the cell line was secreting a spectrum of proteins similar to that found in fetal pig serum (FIG. 15A). No secretion was seen in STO feeder-cells alone (not shown; Talbot et al. 1994, 2000a, 2005, supra). Several of the protein spots were identified by MALDI-TOF and LC-MS/MS mass spectroscopy. The serum-proteins identified included alpha-2-HS-glycoprotein precursor (fetuin-A), transthyretin, albumin, alpha-fetoprotein (AFP), transferrin, apolipoprotein-A1, and retinol-binding protein (FIG. 15A and Table 2). The Coomassie Blue total protein staining indicated that transferrin, AFP, alpha-1-anti-trypsin, and fetuin-A were the most abundantly secreted proteins.

TABLE 2

Serum Proteins Identified in the Conditioned Medium of PICM-19H cells by MALDI-TOF and LC-MS/MS.

| Spot No. | MW | PI | Protein ID | Peptides | SC | MO | expected value | NCBI | ID method |
|---|---|---|---|---|---|---|---|---|---|
| 1 | 76918 | 6.93 | Chain A, porcine serum transferrin | 17 | 23% | 119 | 6.10E−07 | gi|18655907 | Maldi Tof |

TABLE 2-continued

Serum Proteins Identified in the Conditioned Medium of PICM-19H cells by MALDI-TOF and LC-MS/MS.

| Spot No. | MW | PI | Protein ID | Peptides | SC | MO | expected value | NCBI | ID method |
|---|---|---|---|---|---|---|---|---|---|
| 2 | 47164 | 5.54 | alpha-1-antitrypsin [Sus scrofa] | 7 | 20% | 84 | 0.0018 | gi\|975230 | Maldi Tof |
| 3 | 68580 | 5.47 | alpha-fetoprotein [Sus scrofa] | 10 | 14% | 100 | 4.90E−05 | gi\|47523700 | Maldi Tof |
| 4 | 38424 | 5.5 | Alpha-2-HS-glycoprotein (Fetuin-A) | 4 | 12% | 268 |  | gi\|231467 | MS/MS |
| 5 | 15792 | 6.34 | Transthyretin (prealbumin) [Sus scrofa] | 6 | 58% | 380 |  | gi\|975233 | MS/MS |
| 6 | 69366 | 5.92 | Albumin [Sus scrofa] | 15 | 26% | 152 | 3.50E−10 | gi\|833798 | Maldi Tof |
| 7 | 30312 | 5.38 | apolipoprotein A-I | 16 | 54% | 220 | 4.90E−17 | gi\|164359 | Maldi Tof |
| 8 | 21142 | 5.6 | Retinol-Binding Protein (Rbp) | 2 | 11% | 88 |  | gi\|2914422 | MS/MS |
| 9 | 20885 | 5.83 | Alpha-1-acidic glycoprotein | 5 | 27% | 69 | 0.068 | gi\|164302 | Maldi Tof |
| 10 | 27746 | 6.59 | Properdin Factor D (Adipsin) | 8 | 37% | 105 | 1.80E−05 | gi\|1705760 | Maldi Tof |

MW: predicted molecular weight;
PI: predicted isoelectric point;
Peptides: the number of peptides matched;
SC: the percentage of sequence coverage;
MO: MOWSE score;
Expected value: the number of matches with equal or better scores that are expected to occur by chance alone (http://www.matrixscience.com);
NCBI: Accession number;
ID method: mass spectroscopy identification method. The assigned protein of the best matched was given with the species in which it has been identified and its accession number.

Analysis of PICM-19B CM showed the cells are secreting much less protein and that only traces of transferrin, AFP, apolipoprotein-A1 and retinol-binding protein are observable after Coomassie Blue staining (FIG. 15B).

Thus, perhaps the most striking difference found between the two derivative PICM-19 cell lines was in their production of serum proteins. Serum protein production by hepatocytes is a defining characteristic shared by only one other cell type, the extraembryonic visceral endoderm cells of the early mammalian embryo (Junqueira et al. 1992. Basic Histology, Appleton and Lange, Norwalk, Conn., page 406; Talbot et al., 2007, supra). In that the PICM-19H cell line retains this hepatocyte function (as found in the parental ARS-PICM-19 cell line; Talbot et al. 1994a, supra) and it is greatly reduced in the PICM-19B cell line, the PICM-19H cell line is hepatocyte-like, while the PICM-19B cell line is not.

Example 9

Ammonia Clearance and Urea Production Assay

Three nearly confluent T25 flask cultures of PICM-19H or PICM-19B were exposed to glutamine-free Williams-E medium supplemented with 10% FBS, 1 mM ornithine, glucagon (100 ng/ml), 2-mercaptothanol (0.1 mM), HEPES (25 mM), and antibiotics for 72 h. The cells were then exposed to the same base medium with the addition of 12 μmoles ammonium chloride (final concentration=2 mM) for 48 h. Medium was collected, centrifuged at 2000×g to remove cellular debris, and frozen at −80° C. prior to analysis. Ammonia content of experimental (48 h) and initial ($T_0$) media samples was determined spectrophotometrically using a commercial kit (Pointe Scientific, Inc., Canton, Mich., USA) which was modified for use in a microtiter plate reader. A standard curve was prepared in base medium without ammonia. T25 flasks of STO feeder cells only were also assayed to control for their presence in the PICM-19 cultures.

Figure 16:
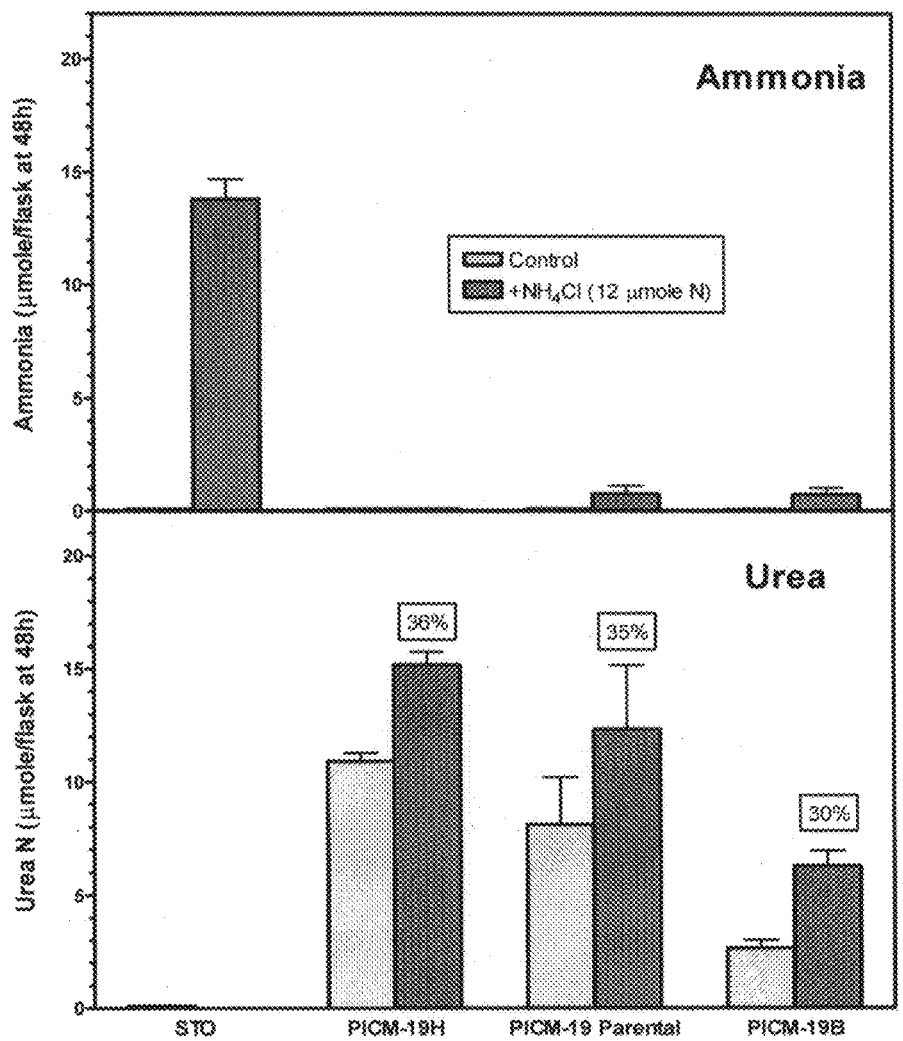
FIG. 16 depicts ammonia clearance and urea production without (control) and with the addition of 12 μmoles of $NH_4Cl$ to the cell culture medium of cultures of the three PICM-19 cell lines tested. The value above each bar is the percentage of added $NH_4Cl$ nitrogen that was converted to urea nitrogen by the cells.

PICM-19H cells are able to completely clear the ammonia added to the cell culture medium of T25 cultures in approximately 24 h (FIG. 16). Both ARS-PICM-19 parental and PICM-19B cells are nearly able to do so, too (FIG. 16). All of the PICM-19 cell lines produce urea from added ammonia with PICM-19H converting 36% of added ammonia nitrogen to urea nitrogen, and PICM-19 parental and PICM-19B achieving 35% and 30% conversion, respectively.

A distinct difference between the two PICM-19 derivative cell lines is in their overall production of urea. In terms of absolute amounts of urea produced on a specific activity basis, PICM-19H produces more than twice as much as PICM-19B (FIG. 16). STO feeder cells alone neither clear added ammonia nor produce urea (FIG. 16). Urea production in response to the addition of 2 mM ammonia on a percent nitrogen conversion basis does not appear to be significantly different between the cell lines. This suggests that the metabolic machinery for urea production from ammonia is intact in the PICM-19B cells, but that it is operating at a lower overall rate. Since it is generally accepted that bile duct epithelium does not produce urea and that it is the function of the hepatocyte (Triebwasser and Freedland. 1977. Biochem. Biophys. Res. Commun. 76: 1159-1165; Jungermann and Katz, 1989. Physiol. Rev. 69: 708-764; Sirica, supra; Van Eyken and Desmet. 1993. Bile Duct Cells. In: Molecular and Cell Biology of the Liver, LeBouton, A. V. (Ed.), CRC Press, Baton Raton, Fla., Pages 475-524; Alpini et al., supra), this finding does not support the classification of the PICM-19B cells as bile duct or gallbladder epithelium. Perhaps like biliary "oval cells" or putative facultative liver stem cells (Newsome et al. 2004. Curr. Top. Dev. Biol. 61: 1-28; Sigal et al. 1992. Am. J. Physiol. 263: G139-148), the PICM-19B cells display a plasticity of function that crosses over between hepatocytes and cholangiocytes.

Example 10

Induction of CYP450 PICM-19H Cells

Assay of Induced Phase I and II Activities

Several CYP450 enzymatic activities were investigated in PICM-19H cells to determine the presence and inducible nature of major CYP450 isoforms. Non-fluorescent substrates were added to cultures of PICM-19H cells (FIG. 17) which were either non-induced controls (containing PBS or 0.1% DMSO) or induced cultures from incubation for 48 h with either 5 µM 3-MC, 50 µM rifampicin (rif) or 1 mM phenobarbital (PHB) to induce CYP450 1A, 3A, and 2, respectively, as described above in Example 7 and is described below. Rifampicin and 3-MC stocks were dissolved in DMSO (0.1% final concentration) and PHB was dissolved in PBS and diluted in growth medium to the final concentration noted above; solvent induction-controls were performed as indicated. Cells were washed with PBS and appropriate inducer medium was added for 48 h prior to experimentation.

CYP450 activity was assessed in T25 cultures of PICM-19H cells that were grown for 3 wk post-passage. T25 cultures of APH or HepG2 C3A cells were tested after 3 d of primary culture and at 1 wk post-passage or near confluency, respectively. Cell cultures were treated for 48 h with an inducing agent, either 3-MC, rifampicin, PHB or DMSO (as a vehicle control). After the initial induction, cells were washed and given a non-fluorescent substrate for CYP1A1, CYP1A2, CYP2, or CYP3A (7-ERF, 7-MRF, MFC, and BFC, respectively). Final incubation conditions were essentially as described by Donato et al. (1993, supra; 2004. *Drug Metab. Dispos.* 32: 699-706), and whole cells were allowed to metabolize substrates 30 min for 7-MRF and 7-ERF, and 60 min for MFC and BFC. Medium samples were collected, centrifuged to remove cell debris (14,000×g, 2 min) and frozen at −80° C. until analyzed. Aliquots of medium samples were added to 96-well plates and the concentrations of fluorescent products were determined (Donato et al. 1993, 2004, supra). Briefly, samples were incubated at 37° C. with or without β-glucuronidase/arylsulphatase (15 Fishman/120 Roy units/ml, Roche Applied Sciences) in pH 4.5 acetate buffer for 2 h to release any fluorescent reaction product that had been conjugated via sulfation or glucurondation phase II conjugation reactions. Standard curves contained resorufin or 7-HFC were treated identically to the experimental medium samples. Fluorescence was determined in an HTS 7000 plate reader; excitation/emission filter pairs were 530/590 and 410/510 for resorufin and 7-HFC, respectively. To determine relative conjugation activity, fluorescence was also determined directly without incubating first in β-glucuronidase/arylsulphatase. Since conjugated forms of resorufin and 7-HFC are non-fluorescent, the difference between the direct and indirect fluorescence measurements represents the amount of product which had been modified by conjugating enzymes.

Protein in cell homogenates, prepared by sonication, was determined by a modified Lowry procedure following NaOH solubilization of TCA-precipitated material (Nerurkar et al., 1981. Quantification of selected Intracellular and Secreted Hydrolases of Macrophages. In: *Manual of Macrophage Methodology*. Herscowitz et al. (eds. Marcel Dekker, Inc., New York, N.Y., pages 229-247). Bovine serum albumin (A6003, Sigma) was used as a standard.

Figure 17:
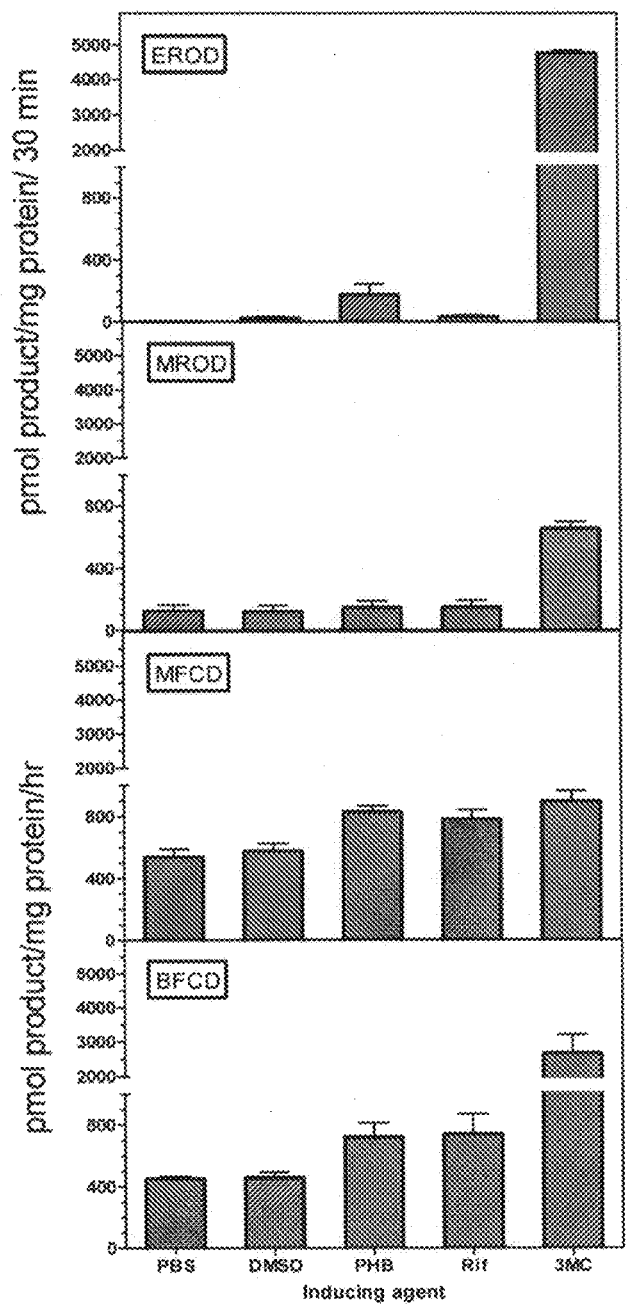
FIG. 17 depicts the induction of multiple CYP450 isoforms in PICM-19H cells with phenobarbital, rifampicin and 3-methylcholanthrene (3-MC). Cultures were exposed to equivalent volumes of PBS, DMSO (0.1% final), 1 mM Phenobarbital (PHB), 50 μM rifampicin (Rif) or 5 μM 3-MC in complete medium. After 48 h, medium was replaced with specific enzyme substrate medium and the activities of the specific CYPs (EROD, MROD, MFCD, and BFCD) were determined. Fresh cultures (n=3) were used for each CYP450 analysis and values are means±SEM of three independent assays.

CYP450 CYP 1A Activity. CYP 1A2 activity, defined here as methoxy resorufin-O-demethylase (MROD) activity, is mainly responsible for metabolizing environmental carcinogens, e.g., polycyclic aromatic hydrocarbons, into their cancer-causing DNA-binding forms (Shimizu et al. 2000. Proc. Nat. Acad. Sci. USA 97:779-782). MROD activity was low in non-induced PICM-19H cultures and in those incubated with PHB and Rif, whereas in those exposed to 3-MC a 5.5-fold induction of activity was measured (FIG. 17). CYP1A1 activity, defined here as ethoxy resorufin-O-deethylase (EROD) activity, is responsible for metabolizing environmental carcinogens, is highly expressed in the liver, and represents ~13% of human liver CYP450 content (Shimada et al., supra). EROD activity was low in non-induced cultures and those induced with Rif, while incubation with PHB and 3-MC resulted in 7- and 198-fold increases in activity, respectively (FIG. 17).

CYP450 CYP2 Activity. The specific activities induced by the addition of PHB and quantified by the conversion of the non-fluorescent MFC to the fluorescent compound 7-HFC are attributable to several members of the CYP2 super family. The activity of CYP2 isoforms referred to here as methoxy trifluoromethyl coumarin demethylase (MFCD) are induced by some xenobiotics and members of the barbiturate family of drugs. In PICM19H cells, MFCD activity was equally induced by PHB, Rif and 3-MC (FIG. 17).

CYP450 CYP3A Activity. In humans, CYP3A4 is responsible for approximately 50% of all drugs metabolized by CYPs (Bertz and Granneman, 1997). In addition to its role in xenobiotic metabolism, CYP3A4 is also important in the biosynthesis of several endogenous steroid hormones and is reported to represent approximately 30-40% of total human hepatic CYPs (Shimada et al., supra). The conversion of the non-fluorescent substrate 7-benzyloxy-4-trifluoromethyl coumarin (7-BFC) to the fluorescent compound 7-hydroxy 4-trifluoromethyl-coumarin (7-HFC) was used to quantitatively measure debenzylation (BFCD) activity. Induction of BFCD with Rif and PHB resulted in an approximate 50% increase in activity compared to non-induced controls, while 3-MC incubation was associated with a 5.8-fold induction (FIG. 17).

Example 11

Liquid Chromatography-Mass Spectrometry of Testosterone Metabolites

Testosterone is hydroxylated by several CYP450 isozymes to yield different metabolite derivatives (Watanabe et al. 1997. *J. Mass Spectrom Soc. Jpn.* 45: 367-375; Donato et al. 1999, supra). PICM-19H cells were treated with 0.1% DMSO or 50 uM Rif for 48 h, followed by a 1 h exposure to 250 µM testosterone (Sigma). Protein was removed from samples by acetonitrile:precipitation (1:1 v/v on ice, 15 min), followed by centrifugation at 10,000×g. Supernatants were taken to dryness under $N_2$ at 37° C., followed by resuspension in 1:1 ethanol:MAF solution (25% methanol, 75% 2 mM ammonium acetate, 0.05% formic acid) at 1:2 of original medium supernatant. Samples were separated with an Alliance 2695 Separation Model (Waters, Beverly, Mass.) with a Symmetry C18 column (3.5 µm, 2.1×100 mm with a 2.1×10 mm guard column containing the same packing material (Waters). The initial mobile phase was 40% Solvent A (2 mM ammonium acetate, 0.05% formic acid) and 60% Solvent B (methanol). A linear gradient was run from 0 to 10 min, reaching 100% Solvent B, and held for 3 min, flow rate 0.2 mL $min^{-1}$. An Ultima API-US, Quadrupole-Time of Flight (Q-TOF) mass spectrometer (Waters) equipped with an electro-spray ionization source, was used in the positive mode to characterize isolated metabolites. The capillary voltage was 2.60 kV (T), collision energy 10 eV, cone voltage 35 V, source and desolvation temperatures were 120 and 350° C., respectively. Cone and desolvation gas flows were 40 and 500 L $h^{-1}$, respectively. Testosterone metabolite standards were obtained from Steraloids, Inc. (Newport, R.I.). The concentrations of compounds were calculated based on concurrently run standard curves, summing peak areas for the ionized parent and two fragments.

Figure 18:
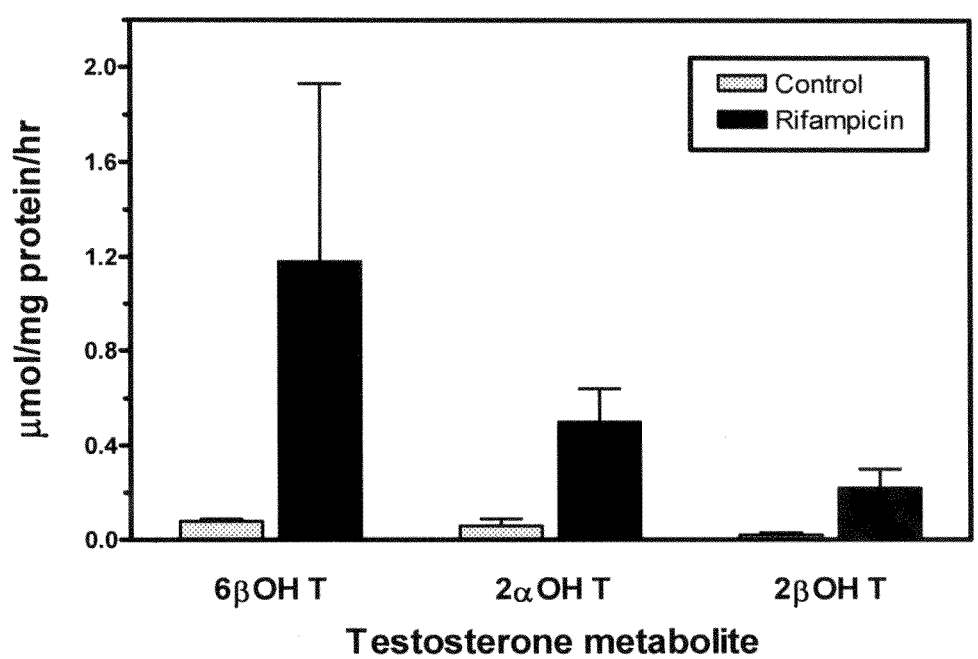
FIG. 18 depicts determination of testosterone metabolites in control and rifampicin-induced PICM-19H cells. Cultures were exposed to 50 μM Rif or 0.1% DMSO for 48 hr and then incubated for 1 h with testosterone. The concentrations of 6-β hydroxy-testosterone (6βOH T), 2-α hydroxyl testosterone (2αOH T) and 2-β hydroxy testosterone (2β OH T) were determined by quantitative LC-MS. Values are means±SEM of three independent experiments which were performed in triplicate cultures.

LC/MS analysis was used to identify and quantify three testosterone metabolites (6βOHT, 2αOHT and 2βOHT) in control and Rif-treated PICM-19Hcultures (FIG. 18). Non-induced activity levels for the production of each metabolite were relatively low (<0.08 umol/mg protein/hr) while induction with Rif was associated with 14.7-, 8.3- and 11-fold increases in the rates of production of 6βOHT, 2αOHT and 2βOHT, respectively (FIG. 18).

While testosterone metabolism in non-induced PICM-19H cultures was negligible, Rif treatment was associated with a greater than 10-fold induction of hydroxylated metabolite formation. As was evident in the PICM-19H cells, pig liver microsomes and fresh pig hepatocytes have also been shown to produce 6β-hydroxylation as the predominant hydroxylated species (Donato et al, 1999). Relatively high induction of 2α- and 2β-hydroxylation activities in the PICM-19H cells was also evident. Interestingly, PICM-19H cells incubated with Rif, metabolized the natural substrate (testosterone) two-to-three orders of magnitude greater than the artificial substrates MFC and BFC, indicating that Rif is indeed capable of inducing high levels of CYP3A activity relative to baseline levels.

Example 12

Comparison of EROD and BCFD Activities with Other Hepatic Cell Types

Figure 19:
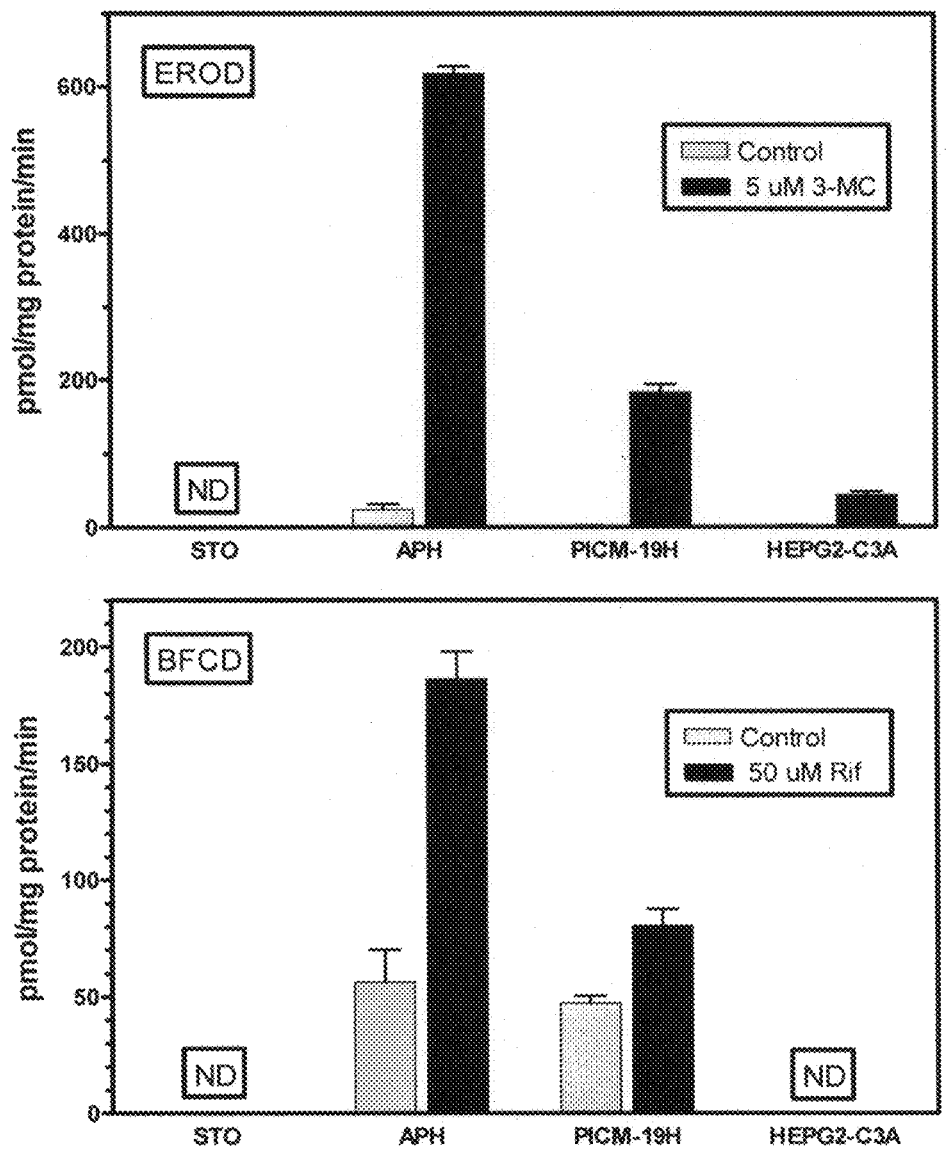
FIG. 19 shows a comparison of CYP450 activities in STO (mouse embryonic fibroblast cell line) cells, adult porcine hepatocytes (APH), PICM-19H cells and human hepatoma-derived HepG2-C3A cells. Triplicate cultures were exposed to 0.1% DMSO (control) and either 50 μM Rif or 5 μM 3-MC for 48 hr and BFCD and EROD activities were determined, respectively. Values are means±SEM of three independent experiments. ND; not detectable.
Figure 20:
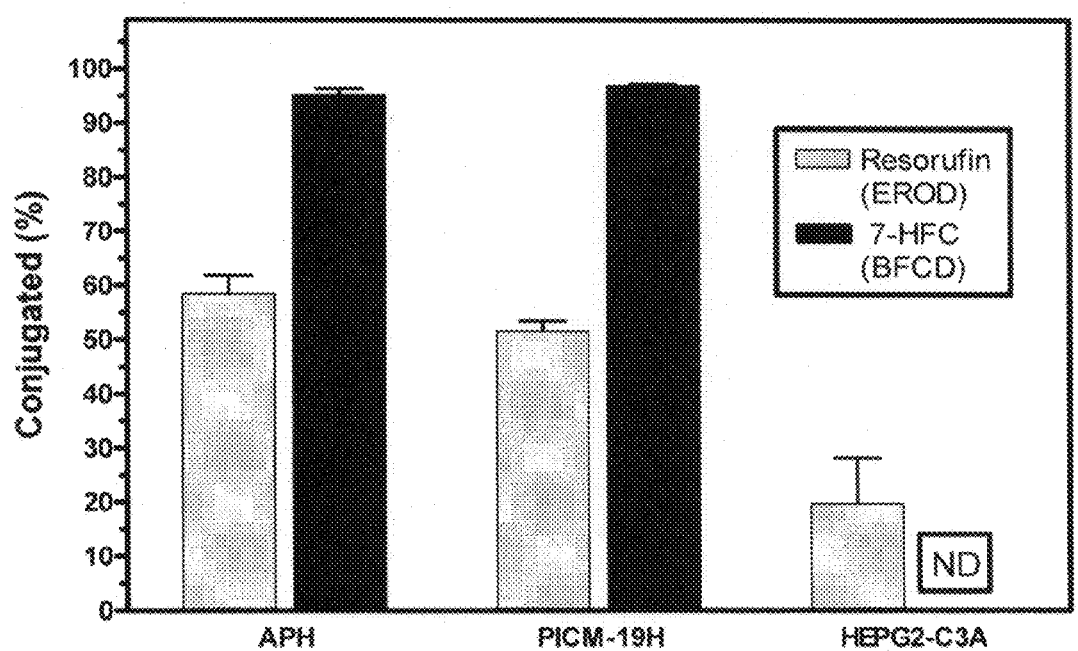
FIG. 20 shows an analysis of Phase II metabolism in adult porcine hepatocytes (APH), PICM-19H cells and HepG2 C3A cells. Activities of induced EROD and BFCD activities were determined with and without incubation of media samples in β-glucuronidase/arylsulfatase cocktail. Fluorescent products (resorufin or 7-HCF) were determined and the amount of product released by the cocktail is reported as a percentage of the total. Values are means±SEM of three independent experiments performed in triplicate cultures. ND; not detectable.

Monolayer cultures of adult pig hepatocytes (APH) and HepG2 C3A cells were prepared and EROD and BCFD activities were compared to PICM-19H cultures following a 48 h induction with 3-MC and Rif, respectively. In addition, we also compared the relative amounts of Phase II activity among the different cell cultures by evaluating the extent to which fluorescent activity was observed before and after treatment with β-glucuronidase/arylsulfatase. As expected, primary cultures of APH demonstrated high levels of inducible EROD and BFCD activities (FIG. 19). Maximal induced EROD and BFCD activities in PICM-19H cells were 30% and 43%, respectively, of that in APH while in HepG2 C3A cells, EROD activity was 7% of APH and BFCD activity was undetectable. STO cells were also evaluated for EROD and BFCD (FIG. 19) and other CYP450 activities and in all cases have demonstrated an absence of detectable activity (not shown). Overall conjugation, or phase II activity, was similar for resorufin and coumarin-based substrates (>50% and >95% conjugation, respectively) for both PICM-19H and APH (FIG. 20). CYP450 was limited to EROD activity in HepG2 C3A cells and only 20% of the resorufin was determined to be in a conjugated form.

Induction of specific substrate metabolism in PICM-19H cells included EROD, MROD, MFCD and BFCD; which correlates with CYP1A1, CYP1A2, CYP2, and CYP3A activities, respectively, at a minimum. 3-MC, at the concentration utilized, induced all of these specific activities. In contrast, PHB induced EROD, and to a lesser extent, BFCD and MFCD activity. Rifampicin was shown to specifically induce MFCD and BFCD, as well as testosterone hydroxylation activities.

In the present study, EROD and BFCD were induced with 3-MC and Rif, respectively, and the activities were compared between freshly prepared APH, a well-characterized human hepatoma cell line, HepG2 C3A, and PICM-19H cells. In comparison to the induced CYP450 activities found in APH cells; PICM-19H had approximately 30% and 43% of the EROD and BFCD activities. In contrast, these activities were low to non-existent in the HepG2 C3A cells. These results were not unexpected. First, in comparison to APH, the PICM-19H cultures are a "naive" population of liver cells in that they are not constantly exposed to the numerous chemical entities that the APH cells are in the in vivo environment of the intact pig's liver. Second, the HepG2 C3A cells are generally recognized to be deficient in certain differentiated hepatocyte functions (Nyberg et al, 1994; Rodriguez-Antona et al 2002), and the C3A derivative cell line appears to share these deficiencies, at least in terms of inducible CYP450s. This comparative lack of differentiated function most likely arises from the fact that the HepG2 cells, unlike PICM-19H cells, are derived from tumor tissue and are abnormal in several growth and differentiation characteristics. For example, 10-14 d after passage, PICM-19H cells stop dividing and by three weeks in culture have terminally differentiated before confluency can be reached. In contrast, HepG2 C3A cells appear to continue to divide even after reaching confluency (data not shown).

Phase II reactions are mediated by cytoplasmic enzymes which are responsible for the detoxification of xenobiotics via conjugation with water-soluble chemical moieties, thus providing a key function for the body's elimination of various chemical entities. With both coumarin- and resorufin-based substrates, PICM-19H cells demonstrated phase II conjugation reactions that were comparable to those of the primary APH cells. Our standard methodology incorporates a combined hydrolytic enzyme preparation, viz., β-glucouronidase/arylsulfatase, so it cannot be readily determined which specific activity was responsible for degradation of the conjugated products as it has been confirmed that sulfation and glucuronidation activities are functional in pig liver tissue (Diaz and Squires. 2003. *Xenobiotica* 33: 485-498) This does not preclude the likely formation of other forms of phase II conjugation such as glutathione addition or acylation reactions, which were not measured in the present study.

Example 13

Cell Viability Assay

The toxic effect of the exposure of cells to chemicals was assayed using the WST-1 cell proliferation reagent (Roche Applied Sciences, Mannhein, Germany). The method measures the conversion of tetrazolium salts to formazan by mitochondrial enzymes in intact cells. A decrease in the production of the formazan dye can be correlated, with a decrease in viable cells compared to controls (Ishiyama et al., supra).

Williams E (Phenol Red-free) supplemented with 2% FCS was used to prepare a 1:10 dilution of WST-1 stock reagent. The diluted reagent was added to the cells and incubated at 37° C. for 30 min. Samples of the cell processed reagent were transferred to a clear 96-well plate, diluted with $dH_2O$ and read in a plate reader (HTS7000, Perkin Elmer, Norwalk, Conn.) at 450 nm. The background at 620 nm was measured and then subtracted from the 450 nm result. Results were compared to untreated controls.

Example 14

Metabolism of Known Hepatotoxins by PICM-19H Cells

Figure 21:
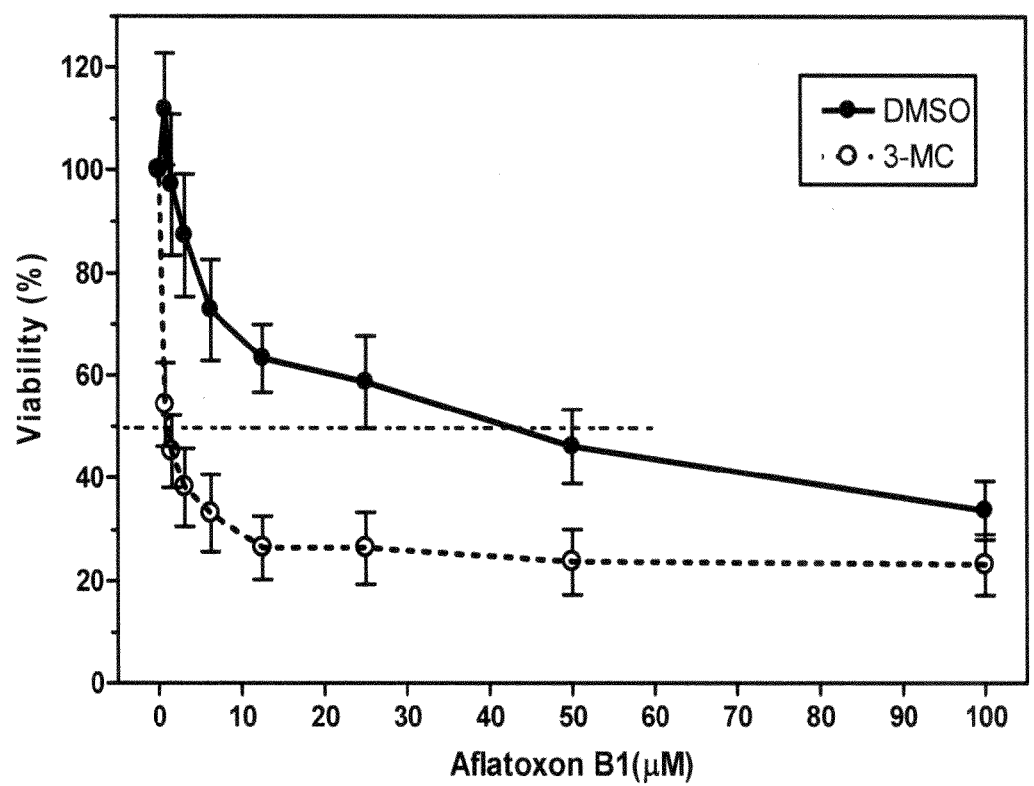
FIG. 21 depicts the bioactivation of aflatoxin B1 in PICM-19H cells. Toxicity of aflatoxin B1 was determined in 0.1% DMSO-treated (control) and 3-MC-induced PICM-19H cells grown in 96-well microplates. Following addition of aflatoxin B1, viability was determined by WST-1 activity in each well. Each concentration of aflatoxin was added to ten wells for each condition. Pooled response curves were analyzed by non-linear regression; exponential model $R^2$ values for DMSO and 3-MC-treated cultures were 0.967 and 0.998, respectively.

Aflatoxin B1 is a well documented mycotoxin and suspected hepatic carcinogen which is metabolized by several CYP450s to generate significantly toxic metabolites (Kamdem et al. 2006. *Chem. Res. Toxicol.* 19: 577-586). In PICM-19H cells grown in 96-well plates, the 50% lethal concentration ($LC_{50}$) of aflatoxin B1, as measured by WST-1 viability, was approximately 40 µM (FIG. 21). The induction of CYP450s with 3-MC was associated with a marked decrease in the $LC_{50}$ (1.1 µM). Thus, 3-MC treatment increased the toxicity of aflatoxin B1 confirming induction of CYPs which are involved in the bioactivation of this toxin.

Figure 22:
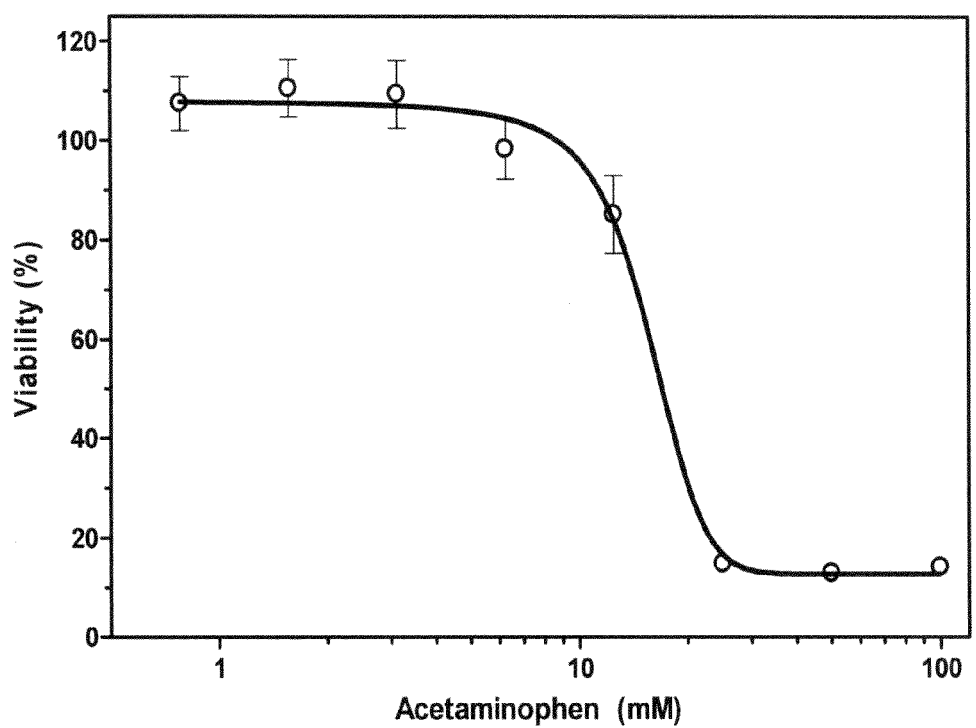
FIG. 22 shows the toxicity determination of acetaminophen in PICM-19H cells. Toxicity of acetaminophen was determined by WST-1 activity in PICM-19H cells grown in 96-well microplates. Nine independent dose response curves were prepared and analyzed by nonlinear regression using a sigmoidal response curve model.

To determine the relative toxicity of acetaminophen in PICM-19H cells, cultures prepared and maintained in 96-well plates were exposed to various concentrations of the drug between 0.78 and 100 mM for 24 h. Viability of PICM-19H cells was determined by WST-1 assay. Regression analysis of ten independent determinations indicated that the $LC_{50}$ for acetaminophen was 12.65±0.75 mM (FIG. 22).

The hepatic CYP450 system is associated with detoxification of absorbed xenobiotics, as well as the metabolism of endogenous molecules including cholesterol and associated steroids. In addition, the CYP450 enzymes can metabolize drugs to more active forms and sometimes into toxic forms. For example, dose-dependent cytotoxicity following treatment of hepatocytes with acetaminophen resulted from the cells generating reactive oxygen species in response, and thereby causing a cytotoxic effect in the hepatocytes (Michael et al. 1999. *Hepatology* 30: 186-195). The $LC_{50}$ of acetaminophen for PICM-19H cells was determined to be approximately 13 mM. This $LC_{50}$ and the dose-response data are similar to previously published experimental values obtained from cultures of human or rodent primary hepatocytes (Wang et al. 2002. *J. Toxicol. Sci.* 27: 229-237; Allen et al. 2005. *Toxicol. Sci.* 84: 110-119). Also, in preliminary experiments, acetaminophen toxicity was enhanced in glutathione-depleted PICM-19H cells (buthionine sulfoxime-treatment) further demonstrating the presence of the metabolic machinery associated with primary acetaminophen metabolism (data not shown). In addition, the toxic bioactivation of aflatoxin B1 in PICM-19H cells demonstrated their hepatic CYP450 metabolism. The cytotoxicity of aflatoxin B1 is enhanced by the activities associated with CYP1A- and 3A (Gallagher et al. 1996. *Toxicol. Applied Pharmacol.* 141: 595-606), and pretreatment of the PICM-19H cells with 3-MC led to a potentiation in aflatoxin B1 toxicity through an induction of these, and perhaps other CYP450s.

Example 15

Culture of PICM-19H Cells without Feeder Cells

A feeder-cell-independent culture of PICM-19H cells was developed. The STO feeder cells have been replaced by pre-coating the tissue culture flasks with polymerizing bovine collagen type I. The flasks are dried and then stored at 4-8° C. before use. The concentration of the collagen currently used is 0.15 mg/ml in complete PICM-19 medium (10% DMEM/199+; Talbot and Paape); however, various concentrations of collagen can be used. Other species of collagen are also available, e.g., human. Other types of collagen are also routinely used for coating, e.g., collagen IV. The base medium is 10% DMEM high glucose that has been conditioned by STO feeder cells for 6 days. At the end of the conditioning period an equal portion of Medium 199 medium (Talbot et al. 1996, supra) is added to the STO conditioned medium (CM), and 2-mercaptoethanol, 100× nucleoside mix, and fetal bovine serum are also added to bring the CM to equivalency with 10% DMEM/199+ (Talbot and Paape, supra). In addition the following growth factors are added to the basic CM medium: (a) ITS liquid medium supplement—insulin, transferrin, selenium 100× (No. I3146, Sigma Chem. Co., St. Louis, Mo.), (b) Hepatocyte Growth Factor (HGF)-50 ng/ml (eBioscience, Sigma, Becton-Dickinson, and R&D Systems), (c) Insulin-like Growth Factor-1 (IGF-1)-25 ng/ml (R&D Systems, Minneapolis, Minn.), and (d) IGF binding protein-4 (IGFBP-4)-50 ng/ml (R&D Systems, Minneapolis, Minn.). The feeder-independent PICM-19H cultures are currently passaged by exposure to trypsin-EDTA (Talbot et al. 1994a, supra); however, cells can also be passaged by exposure to collagenases. The cultures are refed with fresh complete medium every 2-3 days between passages.

Example 16

Culture of PICM-19H and PICM-19B in a Hollow Bioreactor

Figure 23:
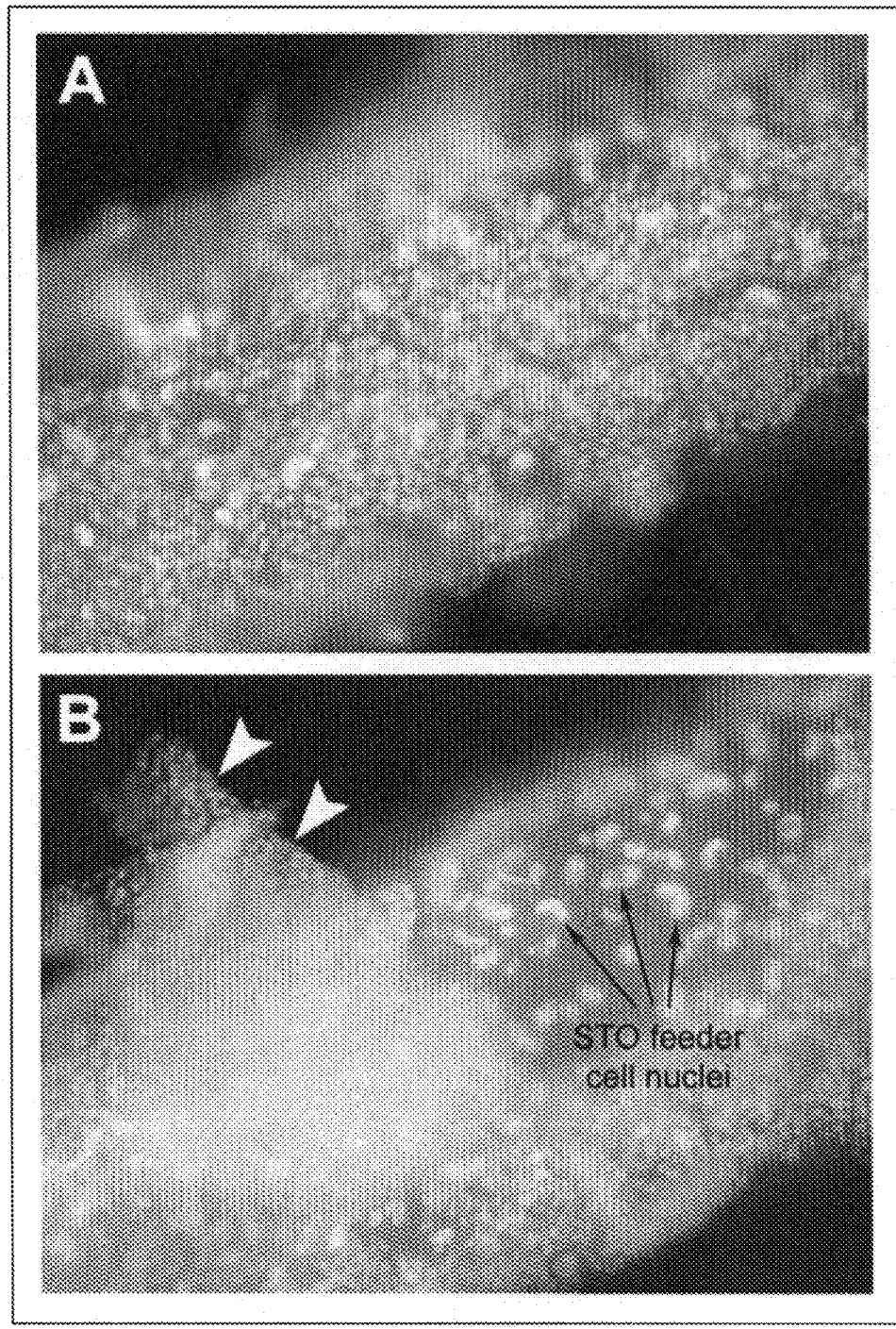
FIGS. 23A and 23B show PICM-19H cells cultured in a 3D-hollow-fiber bioreactor.

PICM-19H and PICM-19B cells were cultured individually or as combined cultures using hollow-fiber bioreactor cartridges. The cells were inoculated with and without STO feeder cells and the PICM cell inoculum consisted of either differentiated cells or undifferentiated cells. The hollow-fiber bioreactors used are of various designs including but not limited to those containing integrated oxygenation fibers (Stem Cell Systems, Berlin Germany). Cells were inoculated in a differentiated or undifferentiated state and cultured using protocols provided by but not limited to various suppliers such as FiberCell, Inc. Frederick Md., USA. The protocols for growth and maintenance of the cells in hollow-fiber culture included but were not limited to continuous recirculation, perfusion and fed-batch modes. The hollow-fiber devices were used without coating or were primed prior to the addition of the PICM-19H and/or the PICM-19B cells by the addition of substances that enhance the attachment of the STO feeder cells (if used) and/or the PICM-19H and/or the PICM-19B cells such as but not limited to collagen in various forms and concentrations. Samples were removed at daily intervals and examined for residual glucose and ammonia levels as well as albumin production. The results of a bioreactor run are shown in FIGS. 23A and 23B.

Example 17

Culture of PICM-19H and PICM-19B on Microcarrier Beads or Encapsulated

Figure 24:
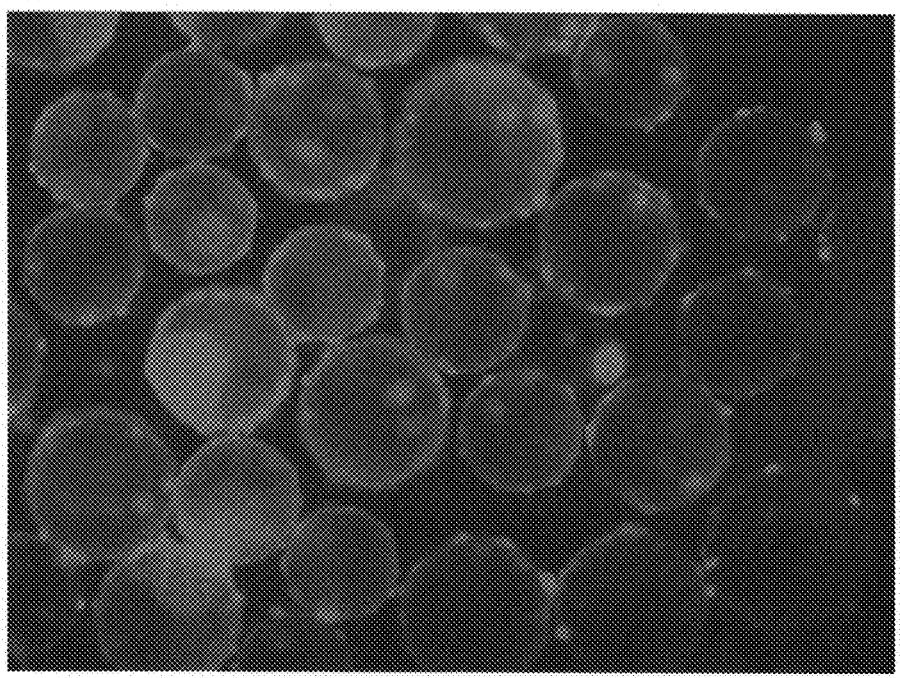
FIGS. 24A and 24B show the PICM-19H cells growing on microbeads in the presence of STO-GFP cells (STO feeder cells expressing green fluorescent protein, GFP). STO-GFP cells were allowed to attach to the beads first; PICM-19H cells were then added to the culture.
Figure 24:
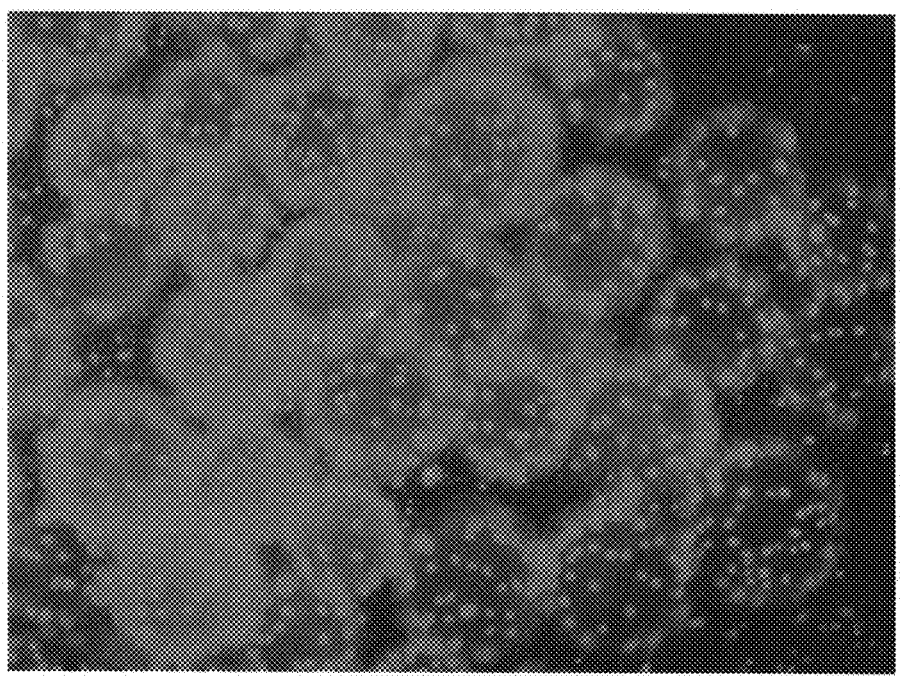

PICM-19H and PICM-19B cells were cultured individually or as combined cultures using microcarrier beads or encapsulated into hydrogels. The cells were inoculated with and without STO feeder cells and the PICM cell inoculum consisted of either differentiated cells or undifferentiated cells. The Microcarrier Beads used were of various designs including but not limited to those containing coatings of bioactive materials and/or surface invagination (SoloHill Engineering Ann Arbor, Mich. USA). Cells were inoculated in a differentiated or undifferentiated state and cultured using protocols provided by but not limited to various suppliers such as those provided by GE Healthcare Piscataway, N.J. USA. The protocols for growth and maintenance of the cells on Microcarrier Beads included, but were not limited to batch, perfusion and fed-batch modes. The Microcarrier Beads were used without coating or were primed prior to the addition of the PICM-19H and/or the PICM-19B cells by the addition of substances that enhance the attachment of the STO feeder cells (if used) and/or the PICM-19H and/or the PICM-19B cells such as but not limited to collagen in various forms and concentrations. Samples were removed at daily intervals and examined for residual glucose and ammonia levels as well as albumin production. The results of a Microcarrier and run are shown in FIGS. 24A and B.

The Hydrogels used for cell encapsulation were of various designs including but not limited to those containing alginate with or without additions of bioactive materials such as collagen. Cells were encapsulated in a differentiated or undifferentiated state and cultured using standard suspension cell techniques or injected into the extracapillary space of a hollow-fiber bioreactor.

Example 18

Culture of PICM-19H as a Spheroid

Figure 25:
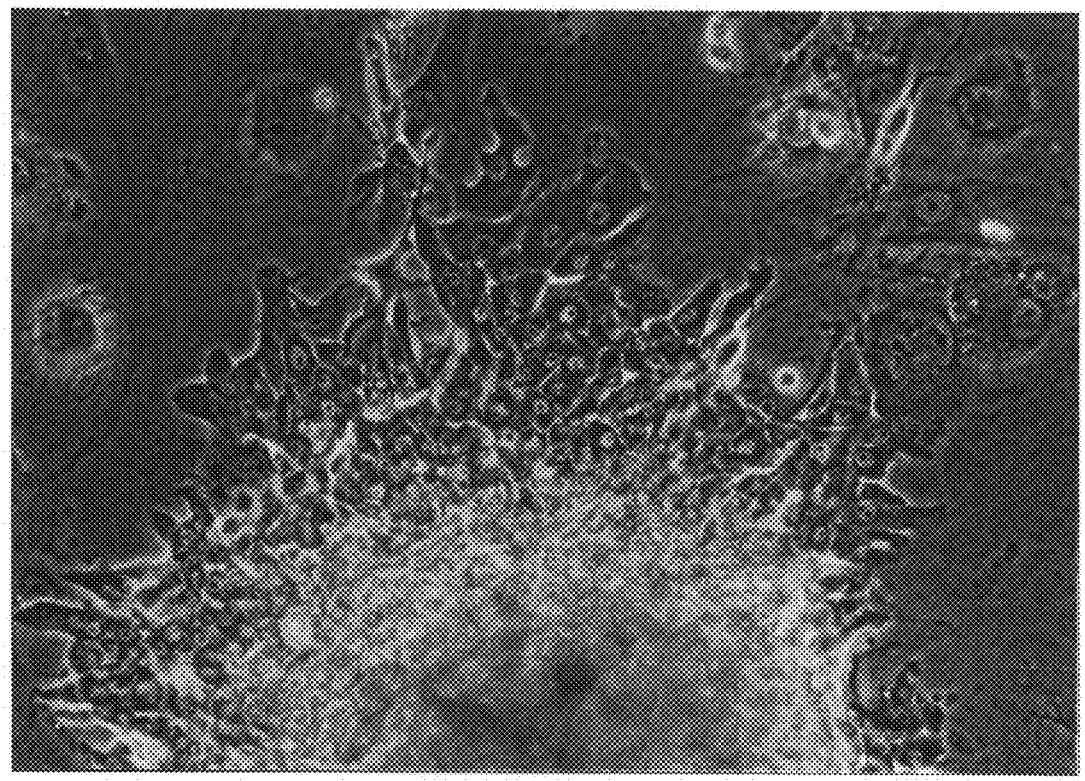
FIG. 25 shows PICM-19H cells grown in culture as a spheroid, a common method of culturing primary pig hepatocytes. The PICM-19H spheroid was cultured for 2 weeks in suspension culture, and then allowed to reattach to a monolayer of STO feeder cells, as shown.

A method with which to create spheroid cultures of PICM-19H cells. PICM-19H cells are released from the tissue culture plasticware by treatment of a PICM-19H culture with collagenase (such as but not limited to collagenase II) prepared in cell culture medium or calcium containing physiological salt solutions (such as but not limited to DMEM or Hank's Buffer Saline Solution) at 1 mg/ml for 15-30 min at 37° C. The collagenase treatment breaks down the collagen fibrils within the culture that is produce by the STO feeder cells and the STO cells and PICM-19H cells retract from each other, the PICM-19H cells forming small balls of cells. The balled up PICM-19H colonies are finally fully released from the plastic substrate by vigorous agitation of the culture flask or by scrapping the culture with a sterile cell scrapper of some type. The balls of PICM-19H cells, nascent spheroids, are suspended in cell culture medium and subjected to low speed centrifugation (e.g. 100-200×g for 5-10 min) and the supernatant above the resulting cell pellet is removed and discarded so as to remove the collagenase. The pellet of nascent PICM-19H spheroids is resuspended in fresh complete culture medium (such as but not limited to 10% DMEM/199; Talbot and Paape, 1996) and cultured with gentle agitation through the use of, but not limited to, a rocking or orbital shaker so that the nascent PICM-19H spheroids do not reattach to the plasticware or plasticware/feeder cell substrate beneath them in the culture vessel. Fresh medium is supplied to the spheroid culture every 2-3 days. The spheroids may be grown and maintained for at least 2 wk by this method as demonstrated in FIG. 25.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated, immortal, unipotent porcine stem cell line wherein cells of said cell line are capable of differentiating exclusively into hepatocytes, wherein the stem cell line is the immortal, unipotent PICM-19 Hepatocyte (PICM-19H) stem cell line deposited as ATCC PTA-9174.

2. The cell line according to claim 1 wherein a culture of said cells further comprises feeder cells.

3. A composition comprising cells of the cell line according to claim 1, said cells being attached to and between single hollow fibers.

4. A bioartificial liver device comprising cells of an isolated, immortal, unipotent porcine stem cell line wherein the stem cell line is the immortal, unipotent PICM-19 Hepatocyte (PICM-19H) stem cell line deposited as ATCC PTA-9174 and a support for said cells.

5. The bioartificial liver device of claim 4, wherein said bioartificial liver device further comprises feeder cells.

6. The bioartificial liver device of claim 4, wherein said support comprises a collection of single hollow fibers, microbeads, or alginate microcapsules.

7. A screening assay kit comprising the immortal, unipotent PICM-19 Hepatocyte (PICM-19H) stem cell line deposited as ATCC PTA-9174.

* * * * *